US012667483B2

(12) United States Patent
Babkin et al.

(10) Patent No.: US 12,667,483 B2
(45) Date of Patent: Jun. 30, 2026

(54) SYSTEMS AND METHODS FOR TREATMENT OF VISCERAL FAT

(71) Applicant: B2M Medical, Inc., Irvine, CA (US)

(72) Inventors: Alexei Babkin, Irvine, CA (US); Rafi Mazor, Irvine, CA (US)

(73) Assignee: B2M MEDICAL, INC., Irvine, CA (US)

( * ) Notice: Subject to any disclaimer, the term of this patent is extended or adjusted under 35 U.S.C. 154(b) by 909 days.

(21) Appl. No.: 17/777,826

(22) PCT Filed: Nov. 20, 2020

(86) PCT No.: PCT/US2020/061568
§ 371 (c)(1),
(2) Date: May 18, 2022

(87) PCT Pub. No.: WO2021/102301
PCT Pub. Date: May 27, 2021

(65) Prior Publication Data
US 2023/0000669 A1     Jan. 5, 2023

Related U.S. Application Data

(60) Provisional application No. 63/028,530, filed on May 21, 2020, provisional application No. 62/938,279, filed on Nov. 20, 2019.

(51) Int. Cl.
*A61F 7/12*       (2006.01)
*A61F 7/00*       (2006.01)
(52) U.S. Cl.
CPC ................ *A61F 7/12* (2013.01); *A61F 7/007* (2013.01); *A61F 7/123* (2013.01);
(Continued)

(58) Field of Classification Search
CPC ............. A61B 18/02; A61F 7/12; A61F 7/123
See application file for complete search history.

(56) References Cited

U.S. PATENT DOCUMENTS

| | | | |
|---|---|---|---|
| 3,674,031 | A | 7/1972 | Weiche |
| 4,447,227 | A | 5/1984 | Kotsanis |

(Continued)

FOREIGN PATENT DOCUMENTS

| | | |
|---|---|---|
| CN | 203425031 U | 2/2014 |
| CN | 115137549 A | 10/2022 |

(Continued)

OTHER PUBLICATIONS

International Search Report and Written Opinion dated Feb. 5, 2021 from IA PCT/US2020/061568.

(Continued)

*Primary Examiner* — Kaitlyn E Smith
(74) *Attorney, Agent, or Firm* — BATT IP A LAW CORPORATION; Richard Batt

(57) ABSTRACT

A system for laparoscopic thermal treatment of visceral fat includes an elongate cooling probe configured for placement through a trocar, the probe including an elongate shaft having a proximal end and a distal end and having a maximum transverse dimension, and an expandable endpiece having a proximal end and a distal end, and including a collapsed state configured for placement through a channel of the trocar and an expanded state, the expanded state having a maximum outer diameter, the maximum outer diameter at least about twice the maximum transverse dimension of the shaft, wherein the proximal end of the endpiece is sealingly coupled to the distal end of the shaft, and a heat exchanger coupled to the cooling probe and configured to remove heat from the endpiece such that adipose tissue placed in contact with the endpiece can be (Continued)

cooled to a temperature of between about 2° C. and about ⁺1° C.

16 Claims, 19 Drawing Sheets

(52) U.S. Cl.
CPC ................. *A61F 2007/0056* (2013.01); *A61F 2007/0075* (2013.01); *A61F 2007/0087* (2013.01)

(56) References Cited

U.S. PATENT DOCUMENTS

| | | | |
|---|---|---|---|
| 5,680,860 A | 10/1997 | Imran | |
| 5,709,679 A * | 1/1998 | Essig ................. | A61B 18/1485 606/41 |
| 6,032,675 A | 3/2000 | Rubinsky | |
| 6,332,089 B1 | 12/2001 | Acker et al. | |
| 6,719,724 B1 | 4/2004 | Walker et al. | |
| 7,141,979 B2 | 11/2006 | Marek | |
| 7,789,849 B2 | 9/2010 | Busby et al. | |
| 9,861,423 B2 | 1/2018 | Lalonde et al. | |
| 9,980,765 B2 | 5/2018 | Avram et al. | |
| 10,667,854 B2 | 6/2020 | Babkin et al. | |
| 10,888,366 B2 | 1/2021 | Allison | |
| 2001/0023334 A1 | 9/2001 | Goar et al. | |
| 2003/0220674 A1 | 11/2003 | Anderson et al. | |
| 2005/0131401 A1 | 6/2005 | Malecki et al. | |
| 2006/0036300 A1 | 2/2006 | Kreindel | |
| 2006/0184048 A1 | 8/2006 | Saadat | |
| 2007/0010861 A1 | 1/2007 | Anderson et al. | |
| 2007/0282324 A1 | 12/2007 | Vaska et al. | |
| 2007/0287886 A1 | 12/2007 | Saadat | |
| 2008/0015445 A1 | 1/2008 | Saadat | |
| 2008/0077202 A1 | 3/2008 | Levinson | |
| 2008/0097560 A1 | 4/2008 | Radziunas et al. | |
| 2009/0076498 A1 * | 3/2009 | Saadat ............... | A61B 18/1492 606/41 |
| 2009/0118722 A1 | 5/2009 | Ebbers et al. | |
| 2009/0270851 A1 | 10/2009 | Babkin et al. | |
| 2010/0004506 A1 | 1/2010 | Saadat | |
| 2010/0049186 A1 | 2/2010 | Ingle et al. | |
| 2010/0152824 A1 | 6/2010 | Allison | |
| 2010/0256621 A1 | 10/2010 | Babkin et al. | |
| 2012/0283713 A1 | 11/2012 | Mihalik et al. | |
| 2013/0103019 A1 | 4/2013 | Joye et al. | |
| 2013/0190744 A1 | 7/2013 | Avram et al. | |
| 2013/0317497 A1 | 11/2013 | Edwards et al. | |
| 2014/0188039 A1 | 7/2014 | Andrew et al. | |
| 2014/0277302 A1 | 9/2014 | Weber et al. | |

| | | | |
|---|---|---|---|
| 2015/0289920 A1 | 10/2015 | Burnett et al. | |
| 2015/0328077 A1 | 11/2015 | Levinson | |
| 2017/0007310 A1 | 1/2017 | Rajagopalan et al. | |
| 2018/0085554 A1 * | 3/2018 | Kassab ............. | A61M 25/0084 |
| 2018/0146999 A1 | 5/2018 | Baust | |
| 2020/0061202 A1 | 2/2020 | Guo et al. | |
| 2020/0246054 A1 | 8/2020 | Agha | |
| 2021/0030457 A1 | 2/2021 | Avram et al. | |
| 2021/0077183 A1 | 3/2021 | Basu et al. | |
| 2021/0353351 A1 | 11/2021 | Mazor et al. | |
| 2022/0062033 A1 | 3/2022 | Dabrowiak et al. | |
| 2022/0354687 A1 | 11/2022 | Ward et al. | |
| 2023/0000669 A1 | 1/2023 | Babkin et al. | |
| 2023/0039683 A1 | 2/2023 | Weber et al. | |
| 2023/0210574 A1 | 7/2023 | Babkin et al. | |

FOREIGN PATENT DOCUMENTS

| | | | |
|---|---|---|---|
| EP | 2856986 A1 | 4/2015 | |
| WO | 0228331 A1 | 4/2002 | |
| WO | 2003078596 A2 | 9/2003 | |
| WO | 2008055243 A2 | 5/2008 | |
| WO | 2011100692 A1 | 8/2011 | |
| WO | 2012058430 A2 | 5/2012 | |
| WO | 2013181660 A1 | 12/2013 | |
| WO | 2017197323 A1 | 11/2017 | |
| WO | 2020061202 A1 | 3/2020 | |
| WO | 2021102301 A1 | 5/2021 | |
| WO | 2024196973 A1 | 9/2024 | |
| WO | 2025042794 A1 | 2/2025 | |

OTHER PUBLICATIONS

U.S. Appl. No. 17/568,207, filed Jan. 4, 2022, Alexei V. Babkin, Entire Document.
U.S. Appl. No. 17/777,826, filed May 18, 2022, Alexei V. Babkin, Entire Document.
First Examination Report of Australian application No. 2019342120, dated Aug. 29, 2024.
International Search Report and Written Opinion by ISA/US of PCT/US2019/051746, Jan. 9, 2020.
International Search Report and Written Opinion by ISA/US of PCT/US22/72511, Aug. 2, 2022.
International Search Report and Written Opinion by ISA/US of PCT/US22/82674, Jun. 14, 2023.
International Search Report and Written Opinion by the ISA/US of PCT/US24/20622, dated Jun. 27, 2024.
International Search Report and Written Opinion by the ISA/US of PCT/US24/42835, dated Dec. 27, 2024.
Second Examination Report of Australian application No. 2019342120, dated Apr. 4, 2025.

* cited by examiner

SYSTEMS AND METHODS FOR TREATMENT OF VISCERAL FAT

BACKGROUND OF THE INVENTION

Field of the Invention

The disclosed and described technology relates generally to the thermal treatment of fat. More specifically, embodiments of the present disclosure relate to systems, devices and methods for cryolipolysis of fat.

SUMMARY OF THE INVENTION

In a first embodiment of the present disclosure, a system for laparoscopic thermal treatment of visceral fat includes an elongate cooling probe configured for placement through a trocar, the probe including an elongate hollow shaft having a proximal end and a distal end and having a maximum transverse dimension, the shaft having a lumen extending between its proximal end and distal end, an expandable cup having a proximal end and a distal end, and including a collapsed state configured for placement through a channel of the trocar and an expanded state, the expanded state having a maximum outer diameter and a maximum inner diameter, the maximum inner diameter at least about twice the maximum transverse dimension of the shaft, wherein the distal end of the cup in its expanded state defines an opening, wherein the proximal end of the cup is sealingly coupled to the distal end of the shaft such that the lumen of the shaft continues into an interior of the cup, and wherein the proximal end of the shaft is configured to be coupled to a negative pressure source such that adipose tissue adjacent the opening of the cup can be sucked into the interior of the cup, and one or more cooling elements carried by the cup and configured to cool the adipose tissue within the interior of the cup to a temperature of between about −20° C. and about +10° C.

In another embodiment of the present disclosure, a system for laparoscopic thermal treatment of visceral fat includes an elongate cooling probe configured for placement through a trocar, the probe including an elongate shaft having a proximal end and a distal end and having a maximum transverse dimension, and an expandable endpiece having a proximal end and a distal end, and including a collapsed state configured for placement through a channel of the trocar and an expanded state, the expanded state having a maximum outer diameter, the maximum outer diameter at least about twice the maximum transverse dimension of the shaft, wherein the proximal end of the endpiece is sealingly coupled to the distal end of the shaft, and a heat exchanger coupled to the cooling probe and configured to remove heat from the endpiece such that adipose tissue placed in contact with the endpiece can be cooled to a temperature of between about −20° C. and about +10° C.

DETAILED DESCRIPTION OF THE ILLUSTRATED EMBODIMENTS

Figure 1:
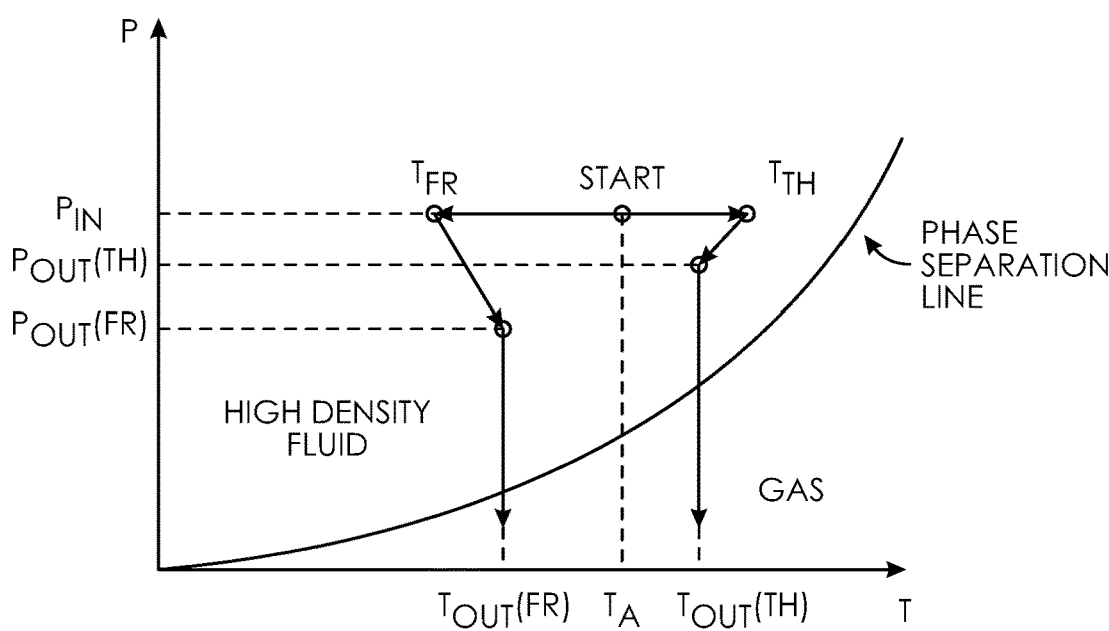
FIG. 1 is thermodynamic phase diagram of a working fluid for use in embodiments of the present disclosure.

The present disclosure relates to systems and methods for treatment of one or more types of human disease by delivering controlled thermal therapy to visceral fat. Visceral fat is an accumulation of intra-abdominal adipose tissue. It is stored within the abdominal cavity and within and around important internal organs such as the intestine, liver, kidneys, heart, stomach, and pancreas. Visceral fat is sometimes known as "deep" fat, and is highly active metabolically. Thus, visceral fat is especially dangerous because it can negatively change the way the body operates.

A person carrying an excess amount of visceral fat is at increased risk of coronary heart disease, hypertension, cancer, stroke, dementia, insulin resistance and diabetes, depression, arthritis, obesity, sexual dysfunction and various sleep disorders. (See Neeb Z, Edwards J, Alloosh M, Long X, Mokelke E, Sturek M, "Metabolic Syndrome and Coronary Artery Disease in Qssabaw Compared With Yucatan Swine," Comparative Medicine (2010) 60:300-15; Despres J, Moorjani S, Lupien P, Tremblay A, Nadeau A, Bouchard C, "Regional Distribution of Body Fat, Plasma Lipoproteins, and Cardiovascular Disease," Arteriosclerosis (1990) 10:497-511; Lemieux I, Pascot A, Prud'homme D, Almeras N, Bogaty P, Nadeau A, Bergeron J, Despres J, "Elevated C-Reactive Protein: Another Component of the Atherothrombotic Profile of Abdominal Obesity," Arteriosclerosis, Thrombosis, and Vascular Biology. (2001) 21:961-67; Pascot A, Lemieux I, Prud'homme D, Tremblay A, Nadeau A, Couillard C, Bergeron J, Lamarche B, Despres J, "Reduced HDL Particle Size as an Additional Feature of the Atherogenic Dyslipidemia of Abdominal Obesity," Journal of Lipid Research (2001) 42:2007-14; Pouliot M, Despres J, Nadeau A, Moorjani S, Prud'homme D, Lupien P, Tremblay A, Bouchard C, "Visceral Obesity in Men. Associations with Glucose Tolerance." Diabetes. 1192; 41(7):826-34; Suzanne L. Doyle, Claire L. Donohoe, Joanne Lysaght, John V. Reynolds. "Visceral obesity, metabolic syndrome, insulin resistance and cancer." Proc Nutr Soc (2012); 71(1):181-9.

Plasma insulin, and Lipoprotein Levels," Diabetes (1992) 41:826-34; Tchemof A, Lamarche B, Prud'homme D, Nadeau A, Moorjani S, Labrie F, Lupien J, Despres J, "The Dense LDL Phenotype. Association With Plasma Lipoprotein Levels, Visceral Obesity, and Hyperinsulinernia in Men," Diabetes Care (1996) 19:629-37; Ross R, Am J, Freeman J, Hudson R, Janssen I, "Abdominal Adiposity and Insulin Resistance in Obese Men," American Journal of Physiology, Endocrinology and Metabolism, (2002) 282: E657-E663; Ross R, Freeman J, Hudson R, Janssen I, "Abdominal Obesity, Muscle Composition, and Insulin Resistance in Premenopausal Women," The Journal of Clinical Endocrinology and Metabolism, (2002) 87:5044-51; Mertens I, Van der Planken M, Corthouts B, Van Gaal L, "Is Visceral Adipose Tissue a Determinant of Von Willebrand Factor in Overweight and Obese Premenopausal Women?" Metabolism: Clinical and Experimental, (2006) 55:650-55; Brunzell J, Hokanson J, "Dyslipidemia of Central Obesity and Insulin Resistance," Diabetes Care, (1999) 22 Suppl 3:C10-C13; Nieves D, Chop M, Retzlaff B, Walden C, Brunzell J, Knopp R, Kahn S, "The Atherogenic Lipoprotein Profile Associated With Obesity and Insulin Resistance is Largely Attributable to Intra-Abdominal Fat," Diabetes, (2003) 52:172-79; Boyko E, Leonetti D, Bergstrom R, Newell-Morris L, Fujimoto W, "Visceral Adiposity, Fasting Plasma Insulin, and Lipid and Lipoprotein Levels in Japanese Americans," International Journal of Obesity and Related Metabolic Disorders, (1996) 20: 801-08.)

Visceral fat is considered toxic and is doubly troubling because it is capable of provoking inflammatory pathways and activates molecules that can interfere with the body's normal hormonal functions. In fact, visceral fat acts like its very own organ because it can have a very large impact on body function as it continuously produces hormones and inflammatory substances. Storing excess fat around the organs increases the production of pro-inflammatory chemicals/substances, while decreasing the levels of protective substances ultimately leading to systemic and tissue inflammation while at the same time, interferes with hormones that regulate appetite, weight, mood, brain function, and other factors. Accordingly, embodiments of the present disclosure are directed to methods, systems and devices that use non-ablative cold temperatures to treat visceral fat and thus reduce or remove its deleterious effect on a patient's health.

Figure 7:
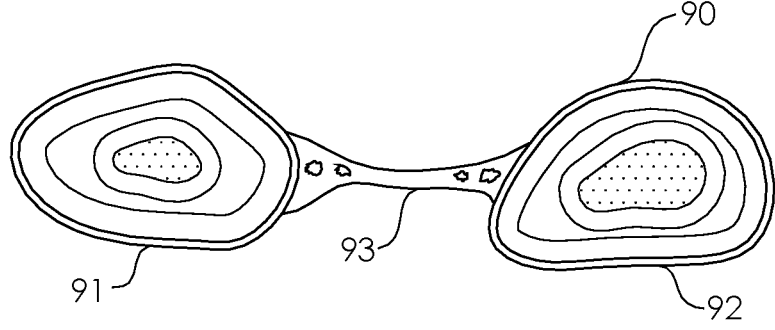
FIG. 7 is a cross-sectional view of healthy human intestine.
Figure 8:
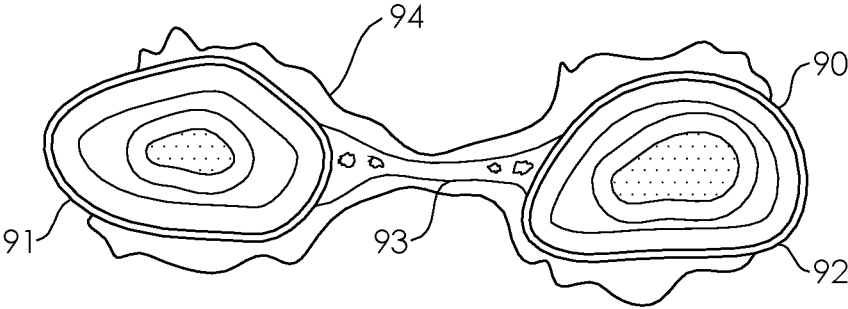
FIG. 8 is a cross-sectional view of human intestine covered by creeping fat.

Accumulating evidence suggests a connection between changes in the mesenteric fat (termed "creeping fat") and inflammatory intestinal diseases including irritable bowel disease (IBD), and Crohn's disease (CD) [Desreumaux P, et al. Inflammatory alterations in mesenteric adipose tissue in Crohn's disease. Gastroenterology 1999; 117:73-81. Schaffler A, et al. Creeping fat in Crohn's disease: traveling in a creeper lane of research? Gut 2005:742-743]. Anatomically, the mesenteric fat is connected with the intestinal serosa and muscularis propria and is continuous along the axis of most of the small and large bowel. Mesenteric fat wrapping (also termed "creeping fat") around the circumference of the intestine is pathognomonic of CD [Coffey J C, et al. The mesentery: structure, function, and role in disease. Lancet Gastroenterol Hepatol 2016; 1:238-247]. It sometimes covers more than 50% of the bowel. FIG. 7 illustrates human intestine 90 in a healthy state. A first portion 91 of the intestine 90 and a second portion 92 of the intestine 90 are held together by mesenterium 93, The mesenterium 93 can also hold the first portion 91 and/or second portion 92 to the dorsal wall of the abdominal cavity (not shown). FIG. 8 illustrates human intestine 90 in a disease state. In addition to the mesenterium 93 providing its connection, creeping fat 94 has covered much of the first portion 91 and second portion 92 of the intestine 90.

Recently, the mesenteric and creeping fat in Crohn's disease has been implicated in its pathogenesis. It contains not only fat cells and their precursors, but also immune cells and non-immune cells, such as endothelial cells and fibroblasts [Mao R, et al. The Mesenteric Fat and Intestinal Muscle interface: Creeping Fat Influencing Stricture Formation in Crohn's Disease. Inflamm Bowel Dis 2019; 25(3): 421-426]. These cell types are activated and creeping fat is now known to be an active participant in inflammation and immunity. Furthermore, creeping fat is associated with muscularis propria hyperplasia and stricturing disease [Borley N R, et al. The relationship between inflammatory and serosal connective tissue changes in Heal Crohn's disease: evidence for a possible causative link. J Pathol 2000; 190:196-202]. Accumulating evidence suggests that modulation of mesenteric fat mass may influence disease. In a retrospective study increased visceral fat area was associated with attenuated mucosal healing after anti-TNT therapy in biologically naïve Crohn's disease patients [Shen W, et al. Visceral Fat Is Associated With Mucosal Healing of Infliximab Treatment in Crohn's Disease. Dis Colon Rectum 2018; 61:706-712]. Visceral adiposity as measured by visceral adipose tissue volume may influence the natural history of disease as shown by an association of increased fat with an increased risk of penetrating disease and surgery in CD [Van Der Sloot K W, et al. Visceral Adiposity, Genetic Susceptibility, and Risk of Complications Among Individuals with Crohn's Disease, Inflamm Bowel Dis 2017; 23:82-88]. Mesenteric fat may influence the perioperative setting as well. Visceral adiposity on cross sectional imaging was found to be an independent risk factor for endoscopic recurrence in postfat cell loss after exposure to cold, even days after the initial cold insult.

Embodiments of system disclosed herein employ an open thermodynamic cycle using a cryogen that is a high-density fluid with a freezing temperature below the treatment temperature. The fluid need not be hazardous (toxic, explosive, etc.) and can take advantage of its high density to serve as an efficient thermal agent. The fluid may also have a relatively low viscosity such that it can flow through small channels and small diameter lumens within the treatment device without a significant pressure gradient and/or viscous heating. Several representative high-density fluids for use in embodiments of the present system are included in Table 1.

TABLE 1

| Fluid | Chemical Formula | Freezing Temperature (Celsius) | Equilibrium Pressure at 25° C. (MPa) | Density (kg/m$^3$) | Viscosity ($\mu$) at $-25°$ C. (Pa · s) |
|---|---|---|---|---|---|
| Alcohol Ethanol | $C_2H_5OH$ | $-114°$ | Stable | 890 | $4.0 \times 10^{-3}$ |
| Octafluoropropane | $C_3F_8$ | $-150°$ | 0.087 | 1500 | $3.6 \times 10^{-4}$ |
| Diethyl Ether | $(C_2H_5)_2O$ | $-116°$ | .100 | 750 | $2.0 \times 10^{-4}$ |
| Propylene Glycol | $C_3H_8O_2$ | $-59°$ | Stable | 1050 | >0.04 | operative Crohn's disease. A causative effect of visceral fat and CD was shown by Coffey et al, who examined surgical recurrence rates after ileocolonic resection for Crohn's disease. In patients with more extensive excision of the mesentery compared to patients with conventional ileocolic resection with limited mesenteric resection, the cumulative reoperation rates were 2.9% and 40% respectively whereas advanced mesenteric disease predicted increased surgical recurrence [Coffey C J, et al. Inclusion of the Mesentery in Ileocolic Resection for Crohn's Disease is Associated With Reduced Surgical Recurrence. J Crohns Colitis 2018; 12:1139-1150].

The present disclosure includes ways to deliver non ablative cold temperatures to the creeping fat as a mean to treat IBD/CD patients, where clinical indications for excessive creeping fat exist. By decreasing the amount of creeping fat we will: reduce the inflammation associated with this tissue in IBD/CD patients; initiate healing of inflamed and ulcerative intestine; prevent the progression and formation of intestinal stenosis (intestinal stricture) and reduce pain associated with Crohn's and IBD. These treatments also refer to patients having Diabetes Mellitus (Type II Diabetes) or who are diagnosed as pre-diabetes status with high levels of visceral/mesenteric fat. Alternatively, these treatments may reduce the risk of developing a chronic disease associated with excess visceral fat.

The scientific premise relies on the fact that fat cells are sensitive to cold temperatures than any other cell type, and fat cell apoptosis can already be detected at temperatures of 10° C. and lower [Manstein D, et al. Selective cryolysis: a novel method of non-invasive fat removal. Lasers Surg Med. 2008 November; 40(9):595-604]. The mechanism that explains fat cells increased sensitivity to cold is that due to their high lipid content, fat cells solidify at a higher temperature compared to other cell types. The freezing temperature of fat is higher than that of water, thus, while other cell types tolerate decreased temperatures, fat solidify and form needle-like crystals in the cell membrane promoting cell death. Inflammation and recruitment of immune cells to the treated site provides additional explanation for increased Depicted in FIG. 1 is a simplified thermodynamic phase diagram of a working fluid used in embodiments of the present disclosure. FIG. 1 illustrates two thermodynamic cycles used in the embodiments of the treatment methods disclosed and described herein: a Freeze Cycle (FC) and Thaw Cycle (TC). In FIG. 1, the X-axis represents temperature (T) and the Y-axis represents pressure (P). Initially, the working fluid is maintained at ambient temperature ($T_A$) and an elevated pressure ($P_{IN}$), as indicated by the word "START." Under these conditions, the fluid would be well within a high-density phase. Some examples of a fluid's high-density phase include a liquid phase and/or a supercritical phase, in which the fluid has the properties of both a liquid and a gas, and which typically occurs above the liquid's critical point (i.e., above the liquid's critical temperature and critical pressure).

Figure 2:
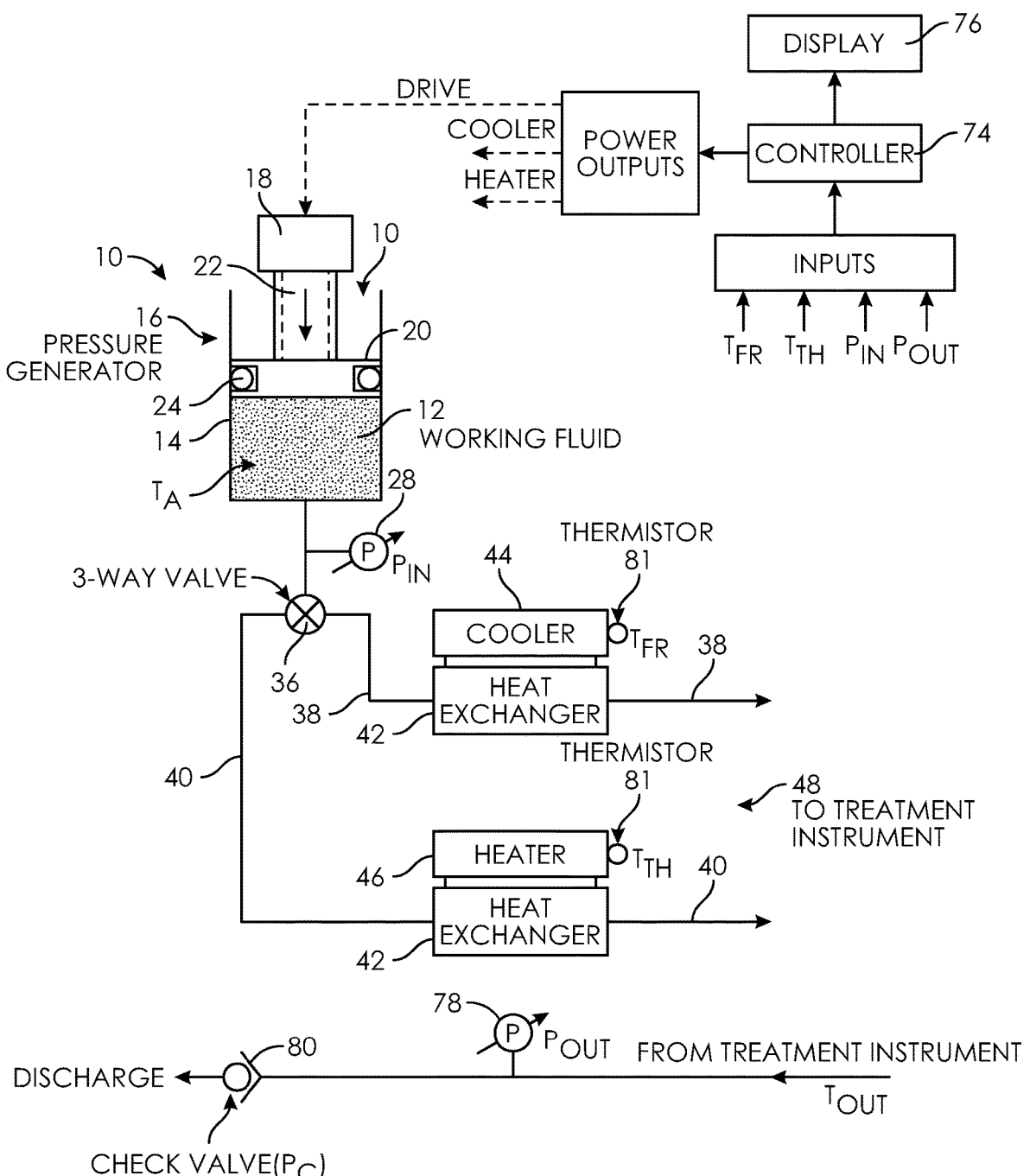
FIG. 2 is a schematic depiction of a system, according to an embodiment of the present disclosure.

An embodiment of a cryotherapy system 10 is depicted in FIG. 2. A thermal fluid/cryogen 12 is held in a container 14 that is maintained at ambient temperature ($T_A$) (See also FIG. 1). A pressure generator 16 is configured to maintain the system 10 at a working pressure. The pressure generator 16 can comprise any device that is capable of creating/generating the required working pressure within the thermal fluid, and capable of maintaining the required pressure for generating the flow rates that are necessary for the system to function. Non-limiting examples of pressure generators are described herein. For example, the pressure generator can be a mechanical piston system that includes a piston head 20, a connecting rod/means 22 and at least one compression ring/gasket 24. The piston head 20 and connecting rod 22 can be driven by, for example, an electrical (stepper) motor (not shown). The pressures necessary to run the system can also be generated and maintained with the use of a closed volume system that contains the working fluid.

Figure 3:
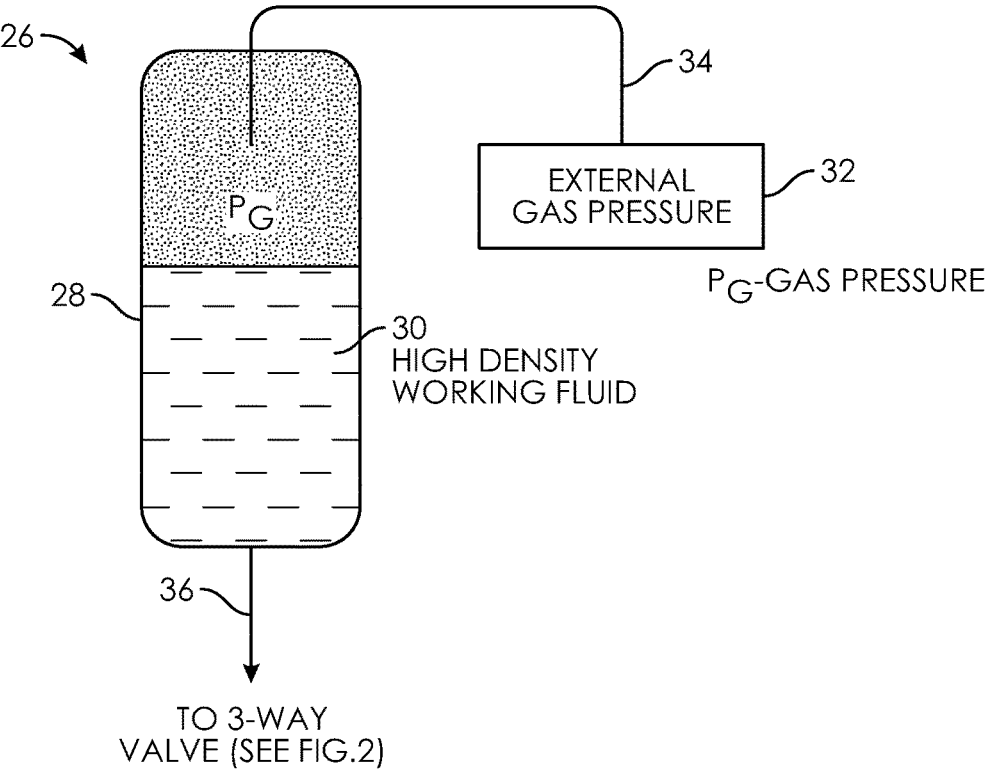
FIG. 3 is a schematic view of a pressure generator, according to an embodiment of the present disclosure.

As depicted in FIG. 3, this type of closed volume system 26 includes a container/tank 28 to hold the working fluid 30, an external gas pressure source 32 and a pressure line 34 that connects the external gas pressure source 32 to the container/tank 28. In this system, pressurizing the external gas pressure source 32 to a certain gas pressure ($P_G$) also causes the working fluid 30 within the container/tank 28 to pressurize to the gas pressure ($P_G$). As will be readily apparent to those skilled in the art, other devices and means can be used to generate the required operating pressures of the system.

Because the system has a dual function of freezing and thawing, a dual fluid flow is utilized. This is achieved with the use of a three-way valve 36 as depicted in FIG. 2. In use, during a freezing cycle, the three-way valve 36 is actuated to a first position to direct working fluid flow along the cooling/freezing flow path 38, and during a thawing cycle, the three-way valve 36 is actuated to a second position to direct working fluid flow along the warming/thawing flow path 40. Thus, the three-way valve is used to control the freeze and thaw cycles of the system.

In an alternative embodiment of this system, the three-way valve can be replaced with a proportional valve, or a combination of proportional valves that enable mixing of (a) cold (or chilled) and (b) hot/warm (or heated) thermal fluids in a chosen proportion, thus achieving any predetermined temperature for the fluid that is to be delivered to a treatment probe.

As can be seen in FIG. 2, both the cooling flow path 38 and the warming flow path 40 include heat exchangers 42 to thermally connect the working fluid to either a cooler 44 (cooling flow path 38) or a heater 46 (warming flow path 40). The cooler 44 can be any type of cooling device capable of achieving and maintaining the required cooling/freezing temperatures. Example coolers 44 include, and are not limited to: thermoelectric coolers (TEC); cryocoolers such as the Pulse Tube (PT), Stirling or Free Piston Stirling Cooler (FPSC), Gifford-McMahon cooler, etc.; Joule-Thomson effect based coolers that use a gas or liquid supply; evaporative coolers such as refrigerators; and an immersion cooler for use with a cryogenic liquid. Another example of a cooler that can be used is an evaporative cooler that relies on cold temperatures that are generated by expansion of the high-density thermal working fluid used in the present system as a result of the pressure drop in the check valve (discussed below). The heater 46 can be any type of a heating device capable of achieving and maintaining the required heating/thawing temperatures. Example heaters 46 include, and are not limited to: a resistive electrical heating element or a thermoelectric heater.

Also included with the system 10 is a treatment instrument 48, or cooling probe, for insertion into the body. The treatment instrument 48 may be configured to be inserted through a trocar for laparoscopic use and may have a cooling tip, which may comprise an expandable endpiece. The treatment instrument 48 connects to the system 10 through a three-port hermetic connector that connects the cold fluid supply line, warm fluid supply line, and a return fluid line from the system 10 to the treatment instrument 48. In some embodiments, multiple cold fluid supply lines and/or multiple warm fluid supply lines and/or multiple return fluid lines may be used. The high-density thermal fluid is configured to rapidly cool and rapidly thaw. Thus, the probe 48 may be removed from the patient quickly and safely after use.

Figure 4:
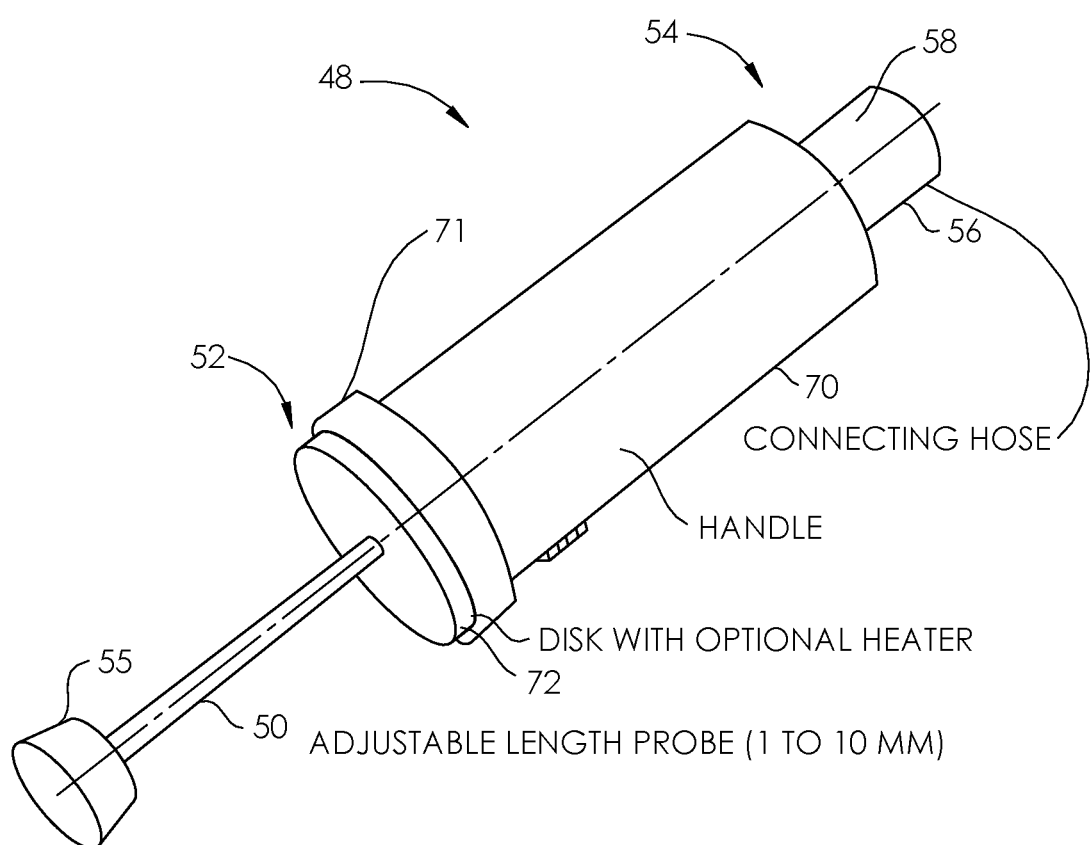
FIG. 4 is a perspective view of a cooling probe, according to a first embodiment of the present disclosure.

Depicted in FIG. 4 is an embodiment of a treatment instrument 48. The treatment instrument 48 includes a shaft 50 extending from its distal end 52. The shaft 50 has a distal end 55 with a flow chamber 53 (see FIG. 5) to allow inflowing working fluid to flow through the treatment instrument 48. The proximal end 54 of the treatment instrument 48 includes a connecting portion 56 for thermally connecting to a supply line/hose 58 from the system 10. In some embodiments, the treatment instrument 48 connects to the system 10 with a supply line/hose 58 that is thermally insulated, having at least two insulated lumens to deliver the high density working/thermal fluid to the treatment instrument 48. A first lumen can be configured to deliver the cooling fluid and a second lumen can be configured to deliver the warming fluid. A third lumen can be configured as a conduit for the return flow, whether it be the return of the cooling fluid or the return of the warming fluid. In some embodiments, the thermal insulation can comprise Aerogel. In other embodiments, it can comprise vacuum insulation. The shaft 50 can comprise a diameter of between about 0.25 mm and about 3 mm and may have a length of between about 1 cm and about 10 cm length.

Figure 5:
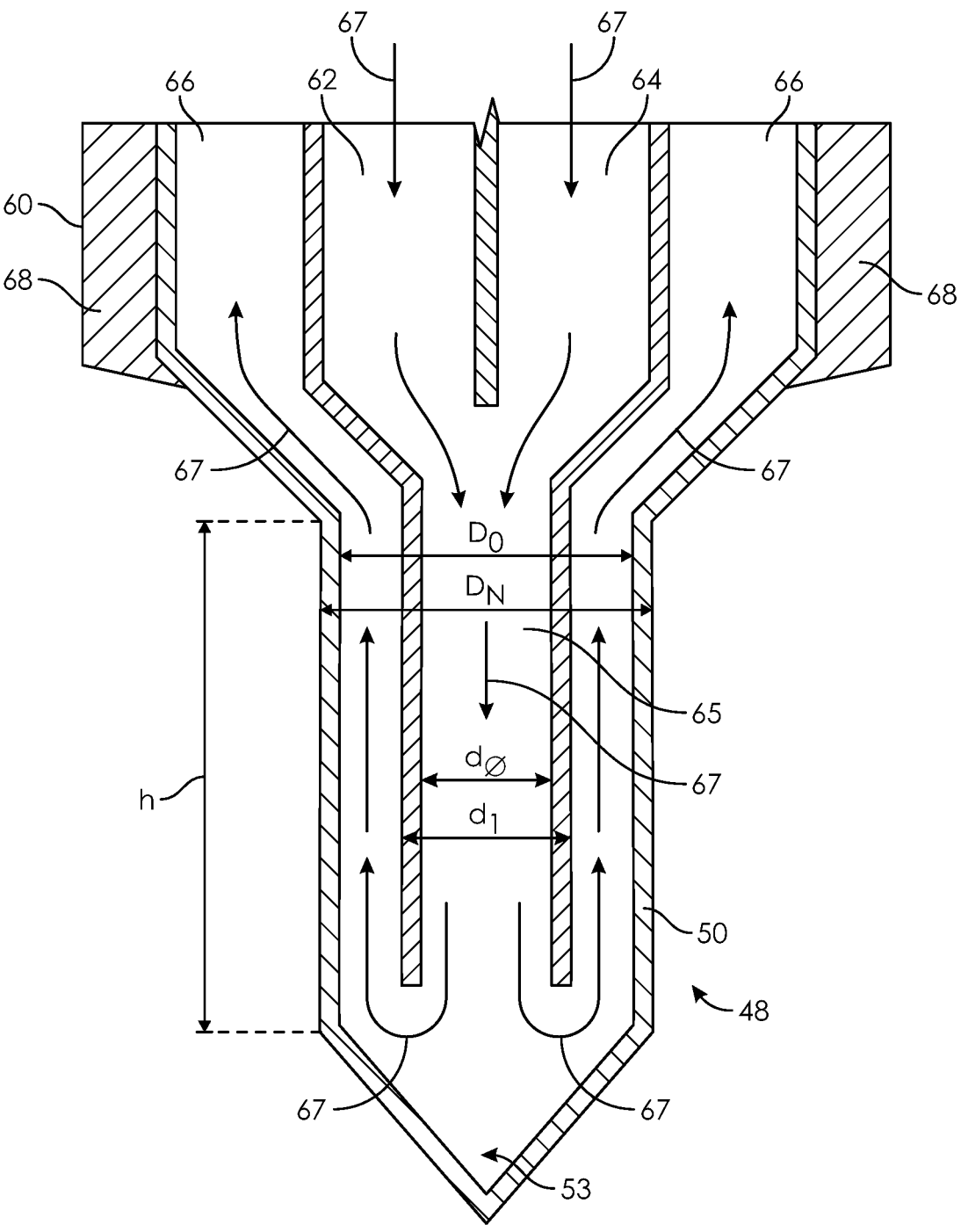
FIG. 5 is a cross-sectional view of a treatment device, according to an embodiment of the present disclosure.

As shown in FIG. 5, the treatment instrument 48 can have a proximal section 60 of a larger diameter in order to house the cooling/freeze channel/lumen 62, the warming/thaw channel/lumen 64 and one or more fluid return channels/lumens 66. The cooling/freeze channel/lumen 62 and the warming/thaw channel/lumen 64 converge distally and open into a single delivery channel/lumen 65 for delivery to the flow chamber 53. Thus, as can be seen in FIG. 5, inflowing working fluid 67 (cooling or heating fluid) flows through either of the cooling/freeze channel/lumen 62 or the warming/thaw channel/lumen 64 depending on the treatment cycle (freezing/thawing), into the delivery channel/lumen 65, into to the flow chamber 53 and then exits the flow chamber 53 by flowing into the return channels/lumens 66. In some embodiments, the proximal section 60 includes thermal insulation (vacuum, Aerogel, etc.) 68 to prevent heat loss and avoid moisture condensation and to prevent freezing/heating along this portion of the treatment instrument 48.

In some embodiments, the shaft 50 extends from a handle portion 70 that, as depicted in FIG. 4, includes a disk-like section 72. The disk-like section 72 is intended to limit the depth that the shaft 50 is inserted into the body of the patient or into the trocar that penetrates the body. The insertion depth can be adjusted using a knob, slider, or a dial 71 located on the handle 70. That is, the knob, slider, or dial 71 can be used to either retract the shaft 50 within the handle 70 thereby changing the length of the shaft 50 that extends from the disk-like section 72. In some embodiments, the knob, slider, or dial 71 can be used move the disk-like section 72 with respect to the shaft 50, which also changes the length of the shaft 50 that extends from the disk-like section 72. Although in the embodiment depicted in FIG. 4, the disk-like section 72 is shown in the form of a disk, the shape is not limited to a disk but can be any shape as long as it can prevent insertion of the shaft 50 past section 72. In some embodiments, the system may include multiple treatment instruments, which may be operated independently of one another or which may be operated synchronously. Accordingly, in these embodiments, the system will include multiple connection ports/supply hoses.

Figure 6:
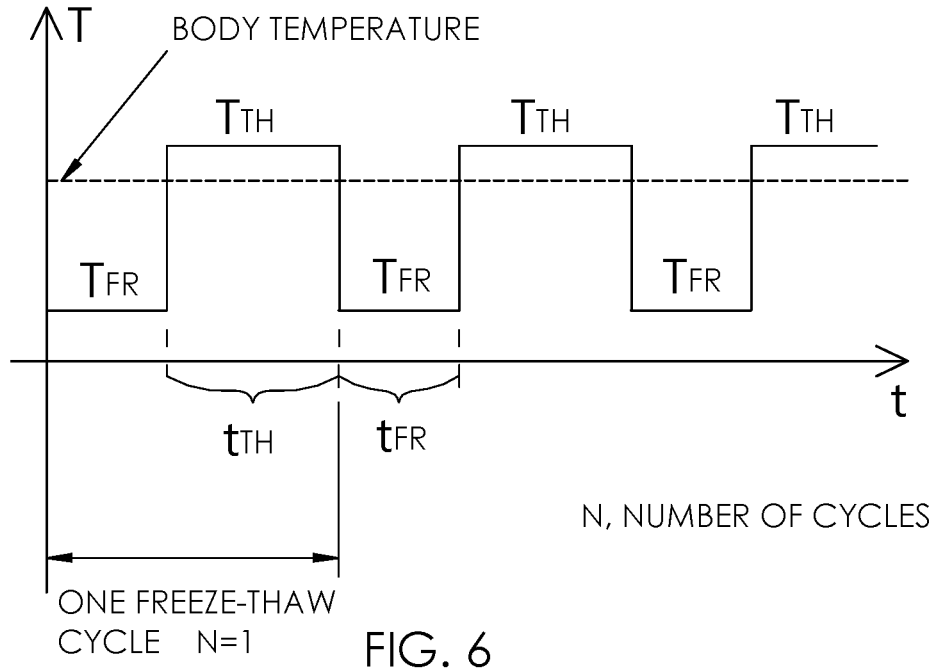
FIG. 6 is a graphic view of treatment cycles, according to an embodiment of the present disclosure.

As depicted in FIG. 2, the system includes a controller/computer 74 for controlling/managing operation of the system 10. With the controller/computer 74, a user can input the operating parameters for the system 10 such as, for example, freeze temperature ($T_{FR}$), thaw temperature ($T_{TH}$), operating pressures ($P_{IN}$, $P_{OUT}$), freeze and thaw cycle run times, treatment cycles (freezing/thawing), number of cycles, treatment instrument operation, etc. The controller/computer 74 can be programmed with the operating parameters for different treatment procedures (as discussed below in more detail). Therefore, depending on the treatment procedure that will be performed, a user can simply choose that procedure from a library of procedures that has been programmed into the controller/computer 74 and the system will operate with the operating parameters that are specific for the subject procedure. The controller/computer 74 also allows a user to modify any such pre-programmed operating parameters for a treatment procedure based on personal preference, experience, treatment area conditions, etc. These modifications or changes to the operating parameters can be performed before a procedure commences or during a procedure based on how the procedure is progressing. Also included is a display 76 for displaying information relating to operation of the system 10 and any additional information essential for the treatment being performed. As depicted in FIG. 6, the treatment cycles of the system 10 comprise alternating periods of freezing ($T_{FR}$) and thawing ($T_{TH}$). Each period is characterized by its temperature (T), duration (t), and the number of duty cycles (N) (for example, a particular period may be described by $T_{FR}$, $T_{TH}$, $t_{FR}$, $t_{TH}$, N). Thus, one cycle may include one freezing ($T_{FR}$) period for a set time ($t_{FR}$) and one thawing ($T_{TH}$) period for a set time ($t_{TH}$). The treatment cycles within one treatment can be identical or they may vary in temperature and/or duration.

In order to regulate the temperature for the freezing and thawing cycles, either of the following methods can be used. The freezing temperature ($T_{FR}$) can be maintained by setting the set temperature for fluid in the cooler 44 to some constant value, −25° C., for example, and regulating the fluid flow by changing pressure $P_{IN}$ of the working fluid flowing from the container 14 to the cooler 44. Similarly, the thawing temperature (Ti) can be maintained by setting the set temperature for fluid in the heater 46 to some constant value, 38° C., for example, and regulating the fluid flow by changing pressure $P_{IN}$ of the working fluid flowing from the container 14 to the heater 46. Alternatively, the freezing temperature ($T_{FR}$) can be maintained by setting the pressure $P_{IN}$ of the working fluid flowing from the container 14 to the cooler 44 to a constant pressure and changing the temperature of the cooler 44. Similarly, the thawing temperature ($T_{TH}$) can be maintained by setting the pressure $P_{IN}$ of the working fluid flowing from the container 14 to the heater 46 to a constant pressure and changing the temperature of the heater 46. Either of the above methods may be used or a combination of the above methods may be used to regulate $T_{FR}$ and $T_{TH}$. The system 10 may also include a plurality of sensors such as pressure gauges 78 and thermistors 81 that are used to monitor operation of the system 10 and to control the operating parameters for treatment procedures. Information obtained from these sensors can be displayed on the display 76 so that a user has real-time operating data for the system. In some embodiments, the system 10 includes a flow meter in the working fluid cooling/freezing flow path 38 in order to measure fluid flow through the system and hence the system's cooling power.

Operation of the system 10 will now be described. The working fluid 12 is first added to container 14, where it is then pressurized by the pressure generator 16 to a predetermined pressure ($P_{IN}$). Next, for a freeze cycle, the three-way valve 36 is actuated to open the flow path 38 to the cooler 44. The working fluid 12 is then delivered to the heat exchanger 42 for the cooler 44 where the working fluid 12 is cooled to a pre-set treatment freeze temperature ($T_{FR}$). Once the working fluid 12 is cooled to $T_{FR}$, the working fluid 12 is delivered the thermally insulated hose 58 (FIG. 4) to the treatment instrument 48, which is positioned such that the shaft 50 delivers the distal end 55 to the target tissue to be cooled/frozen. Because the distal end 55 is in contact with the target tissue, heat is removed from the target tissue by the flowing, cooled working fluid, thereby cooling/freezing the target tissue. Within the treatment instrument/device 48, the working fluid 12 flows into freeze channel/lumen 62 (FIG. 5), into the delivery channel/lumen 65, into to the flow chamber 53, then exits the flow chamber 53 by flowing into the return channels/lumens 66 and then exits the treatment instrument 48 through the return channels/lumens 66. Upon exiting the treatment instrument 48 through the return channels/lumens 66 and return lumen in the thermally insulated hose 58, the return flow of working fluid, which is now at a higher temperature ($T_{OUT}$) and lower pressure ($P_{OUT}$) (FIG. 2) than it was before flowing through the treatment instrument 48, is delivered back to the console, which houses many of the system's components, and discharged to the atmosphere via a check valve 80 that is pre-set to a certain release pressure ($P_C$). Using a check valve with a pre-set release pressure is required in order to maintain the working fluid in its high-density state throughout the freeze cycle. The pre-set release pressure ($P_C$) of the check valve 80 is determined by the choice of working fluid that is used in the system 10. That is, different pressures are required to be maintained for different working fluids in order to maintain the working fluids in their high-density state. it is important to note that from the time the working fluid 12 is pressurized and leaves the container 14 until the time it is discharged to the atmosphere through the check valve 80, the working fluid 12 always remains in its high-density state as can be seen in FIG. 1. The flow rate of the working fluid 12 through the system 10 is determined by the difference between its initial pressure $P_{IN}$ and the pressure $P_{OUT}$.

The thaw cycle is similar to the freeze cycle except that the flow path of the working fluid 12 in the system 10 is different. For the thaw cycle, the three-way valve 36 is actuated to open the flow path 40 to the heater 46. The working fluid 12 is then delivered to the heat exchanger 42 for the heater 46 where the working fluid 12 is heated to a pre-set treatment thaw temperature ($T_{TH}$). Once the working fluid 12 is heated to $T_{TH}$ the working fluid 12 is delivered the thermally insulated hose 58 (FIG. 4) to the treatment instrument 48, which is positioned such that the shaft 50 extends into the target tissue to be heated/thawed. Operation of the system 10 for all other aspects is similar to that of the freeze cycle. Again, as shown in FIG. 1, the working fluid remains in its high-density state at all times during the thaw cycle while flowing in the system 10 until the check valve 80.

In other embodiments, the system can be a closed loop system. As used herein, "closed loop" means that instead of venting working fluid 12 through a check valve 80 to the atmosphere alter it flows through the treatment instrument 48 for either freezing or thawing, the working fluid 12 is instead returned to the holding container 14 for re-use by the system 10. In some embodiments, this can be achieved by means of an external pump (not shown). It is important to note that unlike prior systems (argon-based systems, for example), the cooling/freezing and warming/thawing effect in the present system 10 does not occur at the treatment instrument 48. Instead, cooling and heating of the working fluid 12 are achieved using a dedicated cooler or heater prior to the working fluid 12 entering the treatment instrument 48.

Figures 9, 10:
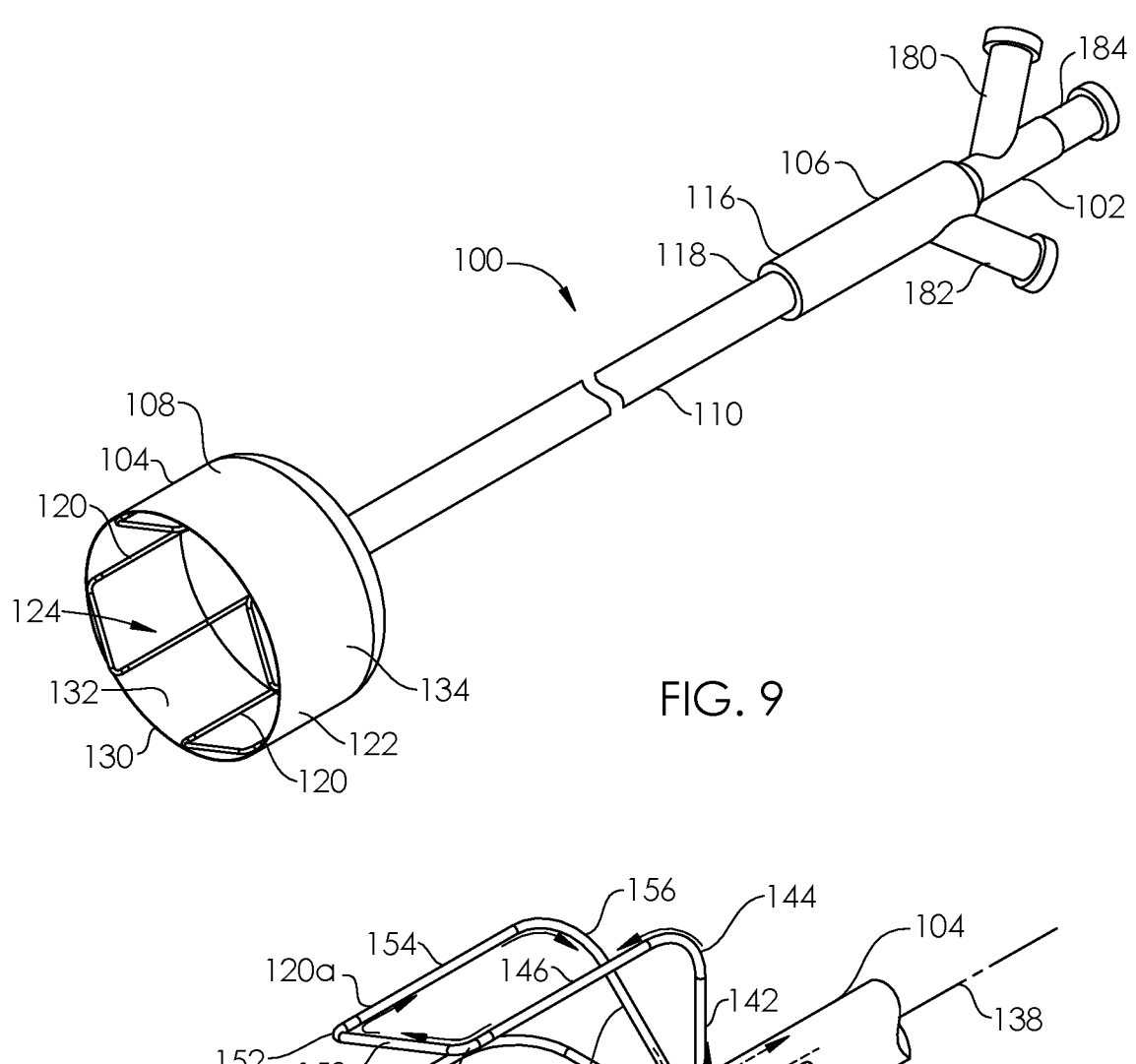
FIG. 9 is a perspective view of cooling probe according to a second embodiment of the present disclosure.
FIG. 10 is a detail view of the distal end of the cooling probe of FIG. 9.
Figures 11, 12, 13, 14:
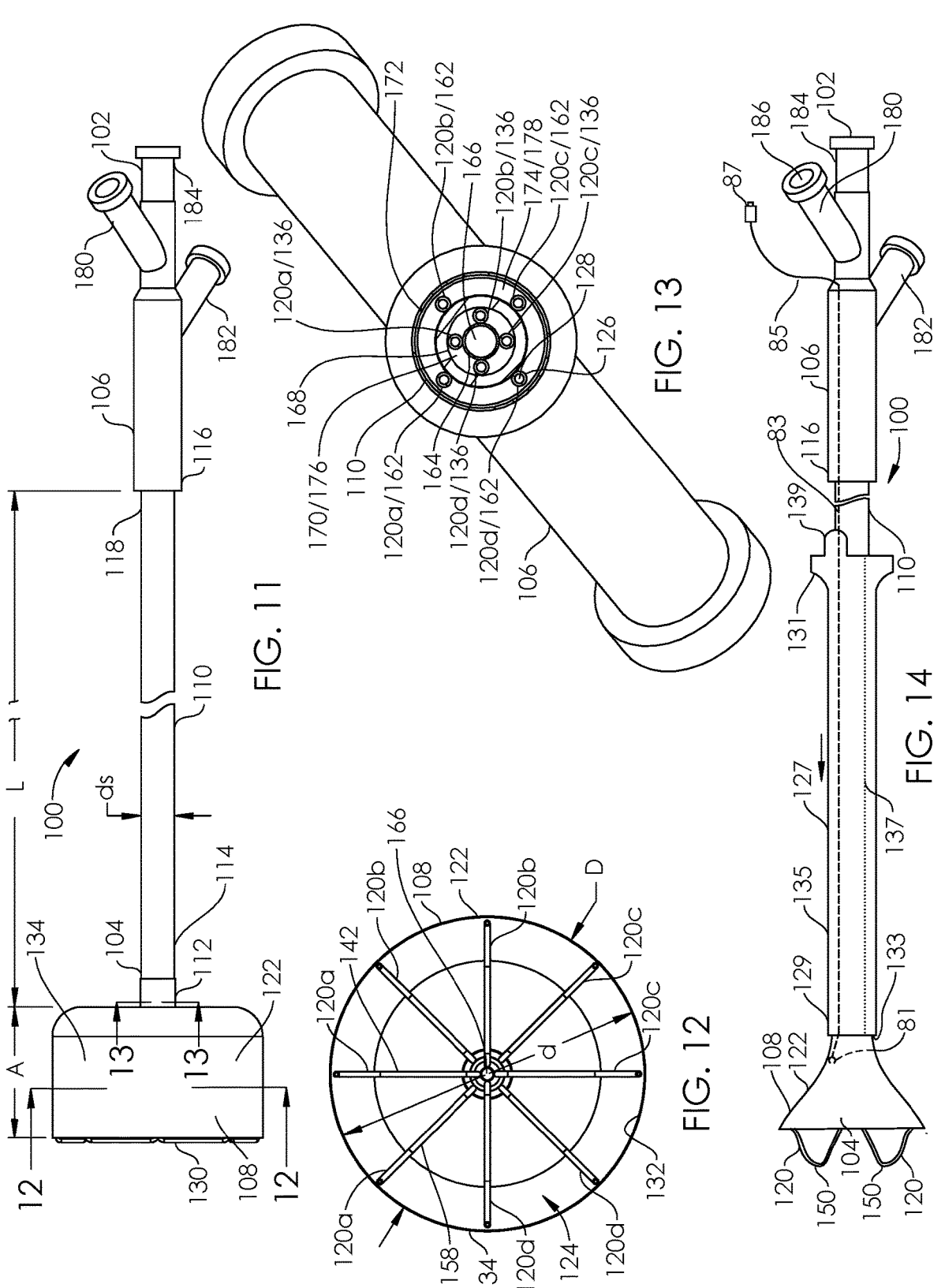
FIG. 11 is a plan view of the cooling probe of FIG. 9.
FIG. 12 is a cross-section view of the cooling probe of FIG. 11 taken along line 12.
FIG. 13 is a cross-section view of the cooling probe of FIG. 11 taken along line 13.
FIG. 14 is a plan view of the cooling probe of FIG. 9 being placed in a collapsed configuration with an introducer, according to an embodiment of the present disclosure.

FIG. 9 illustrates a cooling probe 100 configured for cooling tissue in a patient, including visceral fat. The cooling probe 100 is configured to be placed through the lumen of a trocar that is inserted through the abdominal call of the patient, to perform a cooling procedure laparoscopically. The cooling probe 100 comprises a proximal end 102 and a distal end 104, the proximal end 102 including a connector 106 and the distal end 104 including an expandable cooling cup 108. An elongate shaft 110 is coupled to the cup 108 and the connector 106. As shown in FIG. 11, a proximal end 112 of the cup 108 is secured to a distal end 114 of the shaft 110, and a distal end 116 of the connector 106 is secured to a proximal end 118 of the shaft 110. The shaft 110 may comprise a circular cross-section (as shown), or in other embodiments may comprise a non-circular cross-section (oval, teardrop-shaped, etc.) having a maximum transverse diameter and a minimum transverse diameter. The cup 108 and the connector 106 may each be secured to the shaft 110 by adhesive, epoxy, thermal bonding, shrink tube sealing, tying, or other methods that produce secure attachment. The connector 106 may comprise a molded polymer, such as polycarbonate, acrylic, polyvinyl chloride, or a copolymer including these or other polymers.

Turning to FIGS. 11 and 12, the cup 108 may have a length A of between about 3 mm and about 50 mm, or between about 5 mm and about 35 mm, or between about 8 mm and about 20 mm. The cup 108 may have an outer diameter D between about 6 mm and about 100 mm, or between about 10 mm and about 50 mm, or between about 20 mm and about 40 mm. The shaft 110 may extend a length L of between about 12 cm and about 80 cm, or between about 12 cm and about 30 cm. The shaft 110 may have a diameter ds that is between about 2 mm and about 8 mm. The cup 108 is configured to expand to an expanded configuration (state) that may have an inner diameter d that is at least about twice the diameter ds of the shaft 110. In the expanded state, the cup 108 can have an inner diameter d (and thus an outer diameter D) that is significantly larger than the lumen of a trocar, for example, a 10 mm lumen. The cup 108 includes an interior 124 having a volume V. The volume V of the interior of the cup 108 may be between about 0.65 cm$^3$ and about 393 cm$^3$, or between about 1 cm$^3$ and about 100 cm$^3$. The cup 108 in its collapsed configuration is configured to fit down a 5 mm or 10 mm trocar lumen. Thus, the cup 108 in its collapsed configuration may be configured to have a maximum diameter of 4.8 mm or smaller, or to have a maximum diameter of 9.8 mm or smaller, or generally, a maximum collapsed diameter of between about 3 mm and about 9.8 mm, or between about 7 mm and about 9.8 mm.

The cup 108 comprises four curved cooling tubes 120a-d and an elastic cover 122. In FIG. 10, the elastic cover 122 has been removed to more clearly show the shape and orientation of the cooling tubes 120a-d in the expanded configuration of the cup 108. Each one of the cooling tubes 120a-d is configured to deliver coolant (e.g., thermal fluid) from a first end to a second end of each tube, in order to remove heat from cup 108 and to remove heat from any tissue that is within the interior 124 of the cup 108. A vacuum or suction system will be described that is configured to pull tissue including fat into the interior of the cup 108. The cooling tubes 120a-d each comprise an outer wall 126 and an inner lumen 128 (see FIG. 13). The cooling tubes 120a-d may comprise any material, either metal or polymeric, that provides heat transfer through the outer wall 126. For example, the cooling tubes 120a-d may comprise a high-strength polymeric material such as polyimide, polyamide, or polyester (e.g., PET or PETG) having a thin outer wall to optimize heat transfer. In some embodiments, the polymeric tubes may be heat-shaped to retain memory, and configured to that in their collapsed state they do not significantly overcome their elastic limit. In other embodiments, the polymeric tubes may comprise shape memory polymers that are configured to be changed from their collapsed state to their expanded state by in injection of a heated fluid. Thus, heated thermal fluid may be recirculated through the lumen of the shape memory polymer tubes to cause them to obtain their expanded configuration and then, once this expanded configuration is obtained, cooled thermal fluid may be recirculated through the lumen of the shape memory polymer tubes to provide cooling in the cup 108.

In other embodiments, the polymeric tubes may include coextruded wires in their outer walls 126 such that a curved shape may be placed on them. In some embodiments, the wires may comprise a shape-memory alloy such as a nickel-titanium alloy. In one embodiment, the polymeric tubes with the coextruded wires may be heat set at a preferred shape, such that the wires behave as a superelastic shaped wire that causes the polymeric tubes to conform to their memory shape. The curved tubes may be placed in the collapsed state by placing through a relatively small trocar or catheter lumen, thus straightening the curved tubes while placing the shaped wire in a stress-induced martensitic state. When delivered out of the lumen, the wire moves toward its austenitic state, forcing the memorized curve in the tubes. In other embodiments, the shape-memory characteristics of the wire may be used to change the tubes from their collapsed state to their expanded state by in injection of a heated fluid. Thus, heated thermal fluid may be recirculated through the lumen of the polymer tubes to cause them to obtain their expanded configuration via the heating of the shape-memory wires, causing them to change to their austenitic state. Once this expanded configuration is obtained, cooled thermal fluid may be recirculated through the lumen of the tubes to provide cooling in the cup 108.

In the embodiment shown in FIGS. 9-21, the cooling tubes 120a-d comprise shaped superelastic tubes constructed from a shape-memory alloy such as a nickel-titanium alloy. Thus, the cooling tubes 120a-d perform not only their heat transfer function, but also a function of forming the shape of the cup 108 in its expanded state. The cooling tubes 120a-d, like the embedded wires described above, act as ribs, extending along a surface of the cup 108 from the proximal end 112 to the distal end 130, the one or more ribs configured to help move the cup from its collapsed state to its expanded state. In some embodiments, such as the embodiment shown in FIGS. 9-21, the cooling tubes 120a-d may provide this rib function on their own, while in other embodiments, the cooling tubes 120a-d and additional wire ribs may together serve this function. The additional wires may have a circular cross-section, a rectangular cross-section, or another shaped cross-section. The wires and/or cooling tubes 120a-d may be bonded to an inner surface 132 of the elastic cover 122, or to an outer surface 134 of the elastic cover 122, or some may be bonded to the inner surface 132 while others are bonded to the outer surface 134. If bonded to the outer surface 134, the expansion of the wires and/or cooling tubes 120a-d can be configured to "pull" the diameter of the cover 122 open, or to simply guide the expansion of a pre-sized cover 122. In other embodiments, the wires and/or cooling tubes 120a-d may be left unbonded, and the cover 122 may be configured on the outside of the wires and/or cooling tubes 120a-d, such that expansion of the wires and/or cooling tubes 120a-d automatically stretches the cover 122, to increase its diameter, and retraction or reduction in size of the wires and/or cooling tubes 120a-d automatically allows the cover 122 to retract in diameter. In some embodiments, the wires and/or cooling tubes 120a-d may have a helical shape such that they extended around a circumference of the cover 122 while also extending from the proximal end 112 to the distal end 130 of the cup 108.

The elastic cover 122 may be a general cup shape that is molded, spray-molded, or dip-molded from an elastomer such as silicone, or a thermoplastic elastomer (TPE), such as polyether block amide, or thermoplastic vulcanizate (TPV). The elastic cover 122 may comprise an elastic membrane. The cover 108 in the embodiment of FIG. 9 has a wine glass shape in its expanded state. In other embodiments, the cover 108 may have a basket shape, a generally hemispherical shape, or a generally conical shape. The elastic cover 122 is formed around the outside of the cooling tubes 120*a-d* such that expansion of cooling tubes 120*a-d* automatically stretches the cover 122, to increase its diameter, and retraction or reduction in size of the cooling tubes 120*a-d* automatically allows the cover 122 to retract in diameter. The cooling tubes 120*a-d* may also be bonded to the inner surface 132 of the elastic cover 122 in certain strategic locations. In some embodiments, only one, two, or three bonding points per cooling tube 120 may be used. The cooling tube 120 may be bonded to the inner surface 132 of the cover 122 with a flexible adhesive such as a polyurethane adhesive, or by other adhesives or epoxies. As shown in FIG. 12, the cooling tubes 120*a-d* each define a plane that is transverse to a longitudinal axis of the shaft 110 when the cup 108 is in its expanded state. When the cup 108 is in its collapsed state, the cooling tubes 120*a-d* may also form transverse planes (see FIG. 15), but this is not a requirement, as in some cases, spiraling of the compressed cooling tubes 120*a-d* may actually allow for a smaller collapsed profile. Though four cooling tubes 120*a-d* are shown in the embodiment of FIG. 9, in other embodiments, a single cooling tube or two to twenty cooling tubes, or two to ten cooling tubes may be utilized.

Returning to FIG. 10, a particular fluid flow path is indicated by the arrows in cooling tube 120*a*. Pressurized coolant enters the lumen 128 of the coolant tube 120*a* at a longitudinal inlet end 136 of cooling tube 120*a* in a longitudinal direction, generally parallel to longitudinal axis 138. The coolant follows a first bend 140, changing direction following a first generally radially extending section 142 to a second bend 144 at an outer diameter portion of the cooling tube 120*a*. The first bend 140 may orient the first generally radially extending section 142 substantially 90° from the inlet end 136, or may instead for an obtuse angle, such that the first generally radially extending section 142 also extends slightly distally. The first bend 140 may even be about 120°, or even more. By configuring the first bend 140 slightly larger than 90°, the proximal-to-distal sliding placement of an introducer (described below) may be somewhat facilitated by the forward-leaning angle. At the second bend 144, the coolant changes direction to a first substantially longitudinally extending section 146 (proximal to distal), and moves distally to a third bend 148 an intermediate length 150 and a fourth bend 152. The intermediate length 150 circulates the coolant in a direction generally transverse to the longitudinal axis 138, but it may also have some convex curvature distally. The convex curvature may aid in the controlled, compression and collapse of the cooling tube 120*a*. After the fourth bend 152, the coolant moves along a second substantially longitudinally extending section 154 (distal to proximal) that is reverse of the first substantially longitudinally extending section 146. At a fifth bend 156 in the cooling tube 120*a* the coolant changes direction and moves along a second generally radially extending section 158 back toward the longitudinal axis 138, and then redirects proximally at a sixth bend 160 to a longitudinal outlet end 162. Each of the cooling tubes 120*a-d* may be shaped in this same manner. In the embodiment of FIGS. 9-10, each of the cooling tubes 120*a* is oriented at about 90° from the next around the longitudinal axis 138.

The cooling tubes 120*a-d* are connected to inflow and outflow lumens in the shaft 110 at their inlet ends 136 and outlet ends 162. This can be seen in FIG. 13, and understood fully by also viewing FIGS. 10, 12, and 20-21. An inner tube 164 of the shaft 110 comprises a suction lumen 166. An intermediate tube 168 of the shaft 110 comprises a fluid inlet lumen 170. And, an outer tube 172 of the shaft 110 comprises a fluid outlet lumen 174. The four respective inlet ends 136 of cooling tubes 120*a-d* are bonded in the annulus 176 formed by the fluid inlet lumen 170 outside of the inner tube 164 such that pressurized coolant traveling from a proximal end of the inlet lumen 170 toward the distal end of the inlet lumen enters the lumens 128 of the cooling tubes 120*a-d* at the inlet ends 136. The four respective outlet ends 162 of the cooling tubes 120*a-d* are bonded in the annulus 178 formed by the fluid outlet lumen 174 outside the intermediate tube 168. After the pressurized coolant has traveled completely through the lumens 128 of the cooling tubes, the coolant leaves the lumens 128 at the outlet ends 162 and travels into the fluid outlet lumen 174. The outer portions of the cooling tubes 120*a-d* at the inlet ends 136 and outlet ends 162 are bonded with epoxy or adhesive while protecting the patency of the lumens 128 (with mandrels or other removable materials). In some processes, the banding can be controlled so that no tools are required to temporarily block the lumens 128.

Figure 21:
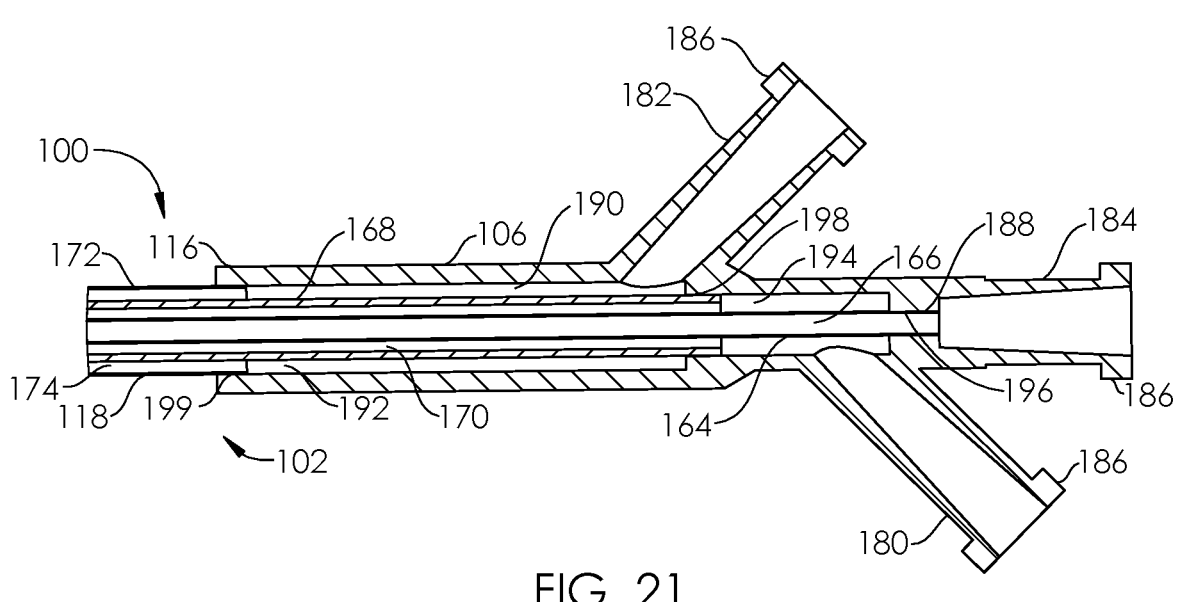
FIG. 21 is a longitudinal sectional view of the proximal connector of the cooling probe of FIG. 9.

Turning to FIG. 21 the connections of the tubes 164, 168, 172 to the connector 106 are illustrated. The connector is shown with an inflow port 180, and outflow port 182, and a suction port 184. Although the three ports 180, 182, 184 are illustrated wherein each comprises a female luer 186 having a male luer-lock, alternatively one or more of the ports 180, 182, 184 may have an alternative structure, such as a barb or an external taper for the placement of friction-fit tubing. The connector has an inner bore 190 having a larger diameter distal portion 192, an intermediate diameter central portion 194, and a smaller diameter proximal portion 196. A proximal end 188 of the inner tube 164 is bonded within the proximal portion 196 of the inner bore 190. A proximal end 198 of the intermediate tube 168 is bonded within the central portion 194 of the inner bore 190. A proximal end 199 of the outer tube 172 is bonded within the distal portion 192 of the inner bore. The bonding of the tubes 164, 168, 172 may be accomplished using epoxy or adhesive, or they may be friction fit. The suction lumen 166 of the inner tube 164 is thus fluidly coupled to the suction port 184. The fluid inlet lumen 170 is fluidly coupled to the inflow port 180. The fluid outlet lumen 174 is fluidly coupled to the outflow port 182. The suction port 184 is configured to be coupled to a suction or vacuum system, such as a vacuum pump. The inflow port 180 is configured to be coupled to a cooling system supplying cooling fluid (coolant), for example, fluid that has been cooled by a heat exchanger. The outflow port 182 is configured to be coupled to the cooling system to return heated coolant to the heat exchanger. The cooling system may comprise any of the heat exchange processes described herein, including but not limited to the cryotherapy system 10 depicted in FIG. 2.

Figures 15, 16, 17, 18, 19:
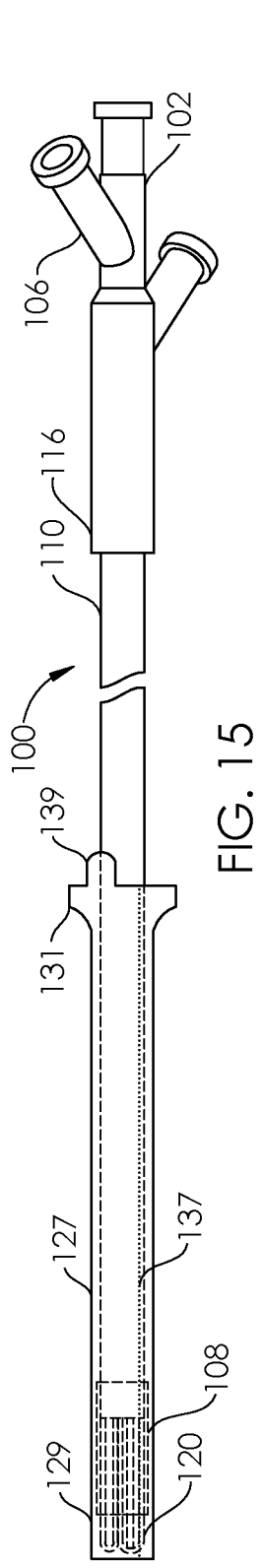
FIG. 15 is plan view of the cooling probe completely within the introducer.
FIG. 16 is a perspective view of a trocar being placed through the abdominal wall.
FIG. 17 is a perspective view of the cooling probe within the introducer and being inserted through the trocar.
FIG. 18 is a perspective view of the cooling probe in an expanded configuration cooling visceral fat adjacent the small intestine.
FIG. 19 is a perspective view of the cooling probe being removed after the procedure.

A laparoscopic procedure for cooling visceral fat is shown in FIGS. 16-17. In FIG. 16, a first trocar 101 comprising a cannula 103 and an obturator 105 is inserted through an abdominal wall 107 of a patient 109 such that the cannula 103 gains access to the abdominal cavity 111 of the patient 109. The obturator 105 is then removed with the cannula 103 automatically sealing at the seal 113. A small intestine 115 of the patient 109 includes a portion of visceral fat 117 to be cryogenically treated. In FIG. 17, a second trocar 119 may be inserted through the abdominal wall 107 to provide insufflation via an insufflation line 121. The space in the abdominal cavity 111 is thus increased. Alternatively, the insufflation may be applied through the first trocar 101. After insufflation, the first trocar 101 may be more safely inserted further into the abdominal cavity 111, as shown in FIG. 17. A third trocar 123 is inserted through the abdominal wall 107 and is used to provide access to a laparoscope 125 for illuminating and viewing the procedure. The trocars 101, 119, 123 may be 5 mm trocars, or 10 mm trocars, or 12 mm trocars depending upon the size requirements of the devices to be placed through the lumens.

Turning to FIG. 14, the cooling probe 100 is shown with a peel-away introducer sheath 127 having a distal end 129 and a proximal end 131. The introducer sheath 127 includes a tubular body 135 with a pre-weakened, scored, or perfo- rated longitudinal line 137. The introducer sheath 127 also includes a holding tab 139, and may be constructed of a lubricious or semi-lubricious polymeric material, such as polyamide, polyester, polyolefin, ETFE, or PTFE. The proximal end 131 is flared to a larger diameter to aid the manipulation of the introducer sheath 127. The introducer sheath 127 is supplied in place on the shaft 110 proximal to the cup 108. The cooling probe 100 may be provided (e.g., sterile) with the cup 108 packaged in its fully expanded configuration. Prior to insertion of the cooling probe 100 into the lumen of the cannula 103 with the introducer sheath, the introducer sheath is moved distally (arrow) as shown in FIG. 14. The lumen 133 of the introducer sheath 127 forces the cup 108 from its expanded configuration toward its collapsed configuration. FIG. 15 illustrates the cooling probe 100 with the cup 108 in its fully collapsed configuration with the introducer sheath 127 completely covering the cup 108 and the entire distal end 104 of the cooling probe 100.

Returning to FIG. 17, the cooling probe 100 and intro- ducer sheath 127 are inserted together through the lumen of the cannula 103. In FIG. 18, the introducer sheath 127 is pulled proximally by the user, e.g. by holding the proximal end 131 and/or the tab 139. Then, by carefully pulling the tab 139 in a transverse direction to the longitudinal axis 138, the introducer sheath 127 is torn longitudinally along the weakened line 137 and is removed. The cooling probe 100 is now advanced by the user so that the cup 108 exits the cannula 103 and is able to expand toward its expanded configuration. As shown in FIG. 18, the cup 108 is placed over a desired portion of visceral fat 117 to be treated, and suction is applied to the suction lumen 166 by connecting or activating suction to the suction port 184 of the connector 106. The visceral fat 117 (and perhaps some amount of adjacent intestinal tissue) is pulled into the interior 124 of the cup 108. The coolant is now circulated through the fluid inlet lumen 170 via the inflow port 180 and through the lumens 128 of the cooling tubes 120a-d, thus removing heat from the cup 108 and from the visceral fat 117 within the cup 108 until the visceral fat 117 is brought to 10° C. or below. By maintaining the visceral fat at a temperature of between about −20° C. and about +10° C. for a period of time, for example, between about 30 seconds and about 10 minutes, the visceral fat can undergo apoptosis while the normal intestinal tissue is protected from significant damage. Fat tends to be more sensitive to lower temperatures than is much of the surrounding normal tissue. Thus, maintaining the visceral fat at the −20° C. to +10° C. range is selective to deactivate the negative effects of the fat, without allowing the adjacent normal tissue to reach temperatures below −20°

C., that may damage them. In FIG. 19, the cooling and the suction are terminated. The cooling probe 100 is pulled back into the lumen of the cannula 103, compressing the cup 108 of the cooling probe 100 toward its collapsed configuration. A treated portion 141 of the visceral fat 117 is shown in FIG. 19.

Figure 20:
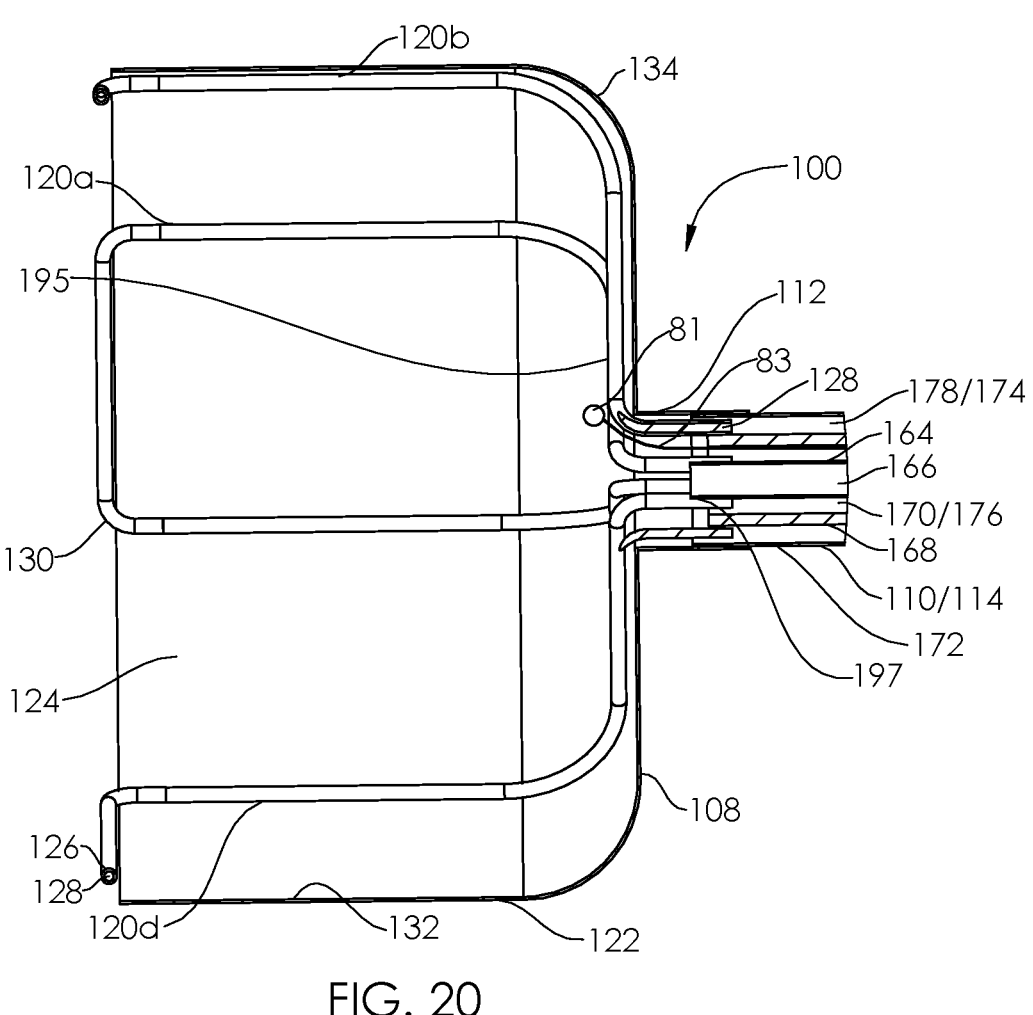
FIG. 20 is a longitudinal sectional view of the distal end of the cooling probe of FIG. 9.

As shown in FIG. 20, the distal end 197 of the inner tube 164 is slightly proximal to the bottom limit 195 of the interior 124 of the cup 108. Thus, the inner tube 164 is less likely to be damaged, and thus the suction lumen 166 is more likely to stay patent as tissue (e.g., visceral fat 117) is sucked into the interior 124 of the cup 108. As long as the suction (negative pressure gradient) is maintained the visceral fat 117 is held in the interior 124 for thermal treatment. As shown in FIGS. 14 and 20, a thermistor 81 extends into the interior 124 of the cup 108 (as shown) or can be just proximal to the bottom limit 195. The thermistor wire 83 extends proximally though any one of the lumens 166, 170, 174, and is configured to carry signals related to temperature sensed by the thermistor 81. The thermistor wire 83 is shown extending through the inlet lumen 170 in this particular embodiment. Alternatively, the thermistor wire 83 may extend through or within the wall of one of the tubes 164, 168, 172 by a composite tubing fabrication method. The proximal end 85 of the thermistor wire 83 is coupled to an electrical connector 87 for attaching to the system 10. The temperature measured by the thermistor 81 in the cup 108 or in the tissue (fat) 177 during cooling can be used to control the amount of cooling (temperature, time) as a feedback loop from the signal sent by the thermistor 81 and received by the system 10 from the connector 87. The feedback loop can be programmed into the controller 74 (FIG. 2) to maintain a treatment temperature T of between about −20° C. and about +10° C., or where −20° C.<T<+10° C., or where −20° C.≤T≤+10° C., or where −20° C.≤T<+10° C., or where −20° C.<T≤+10° C. In alternative embodiments, other types of temperature sensors may be used instead of the thermistor, such as a thermocouple or an RTD.

Figure 22:
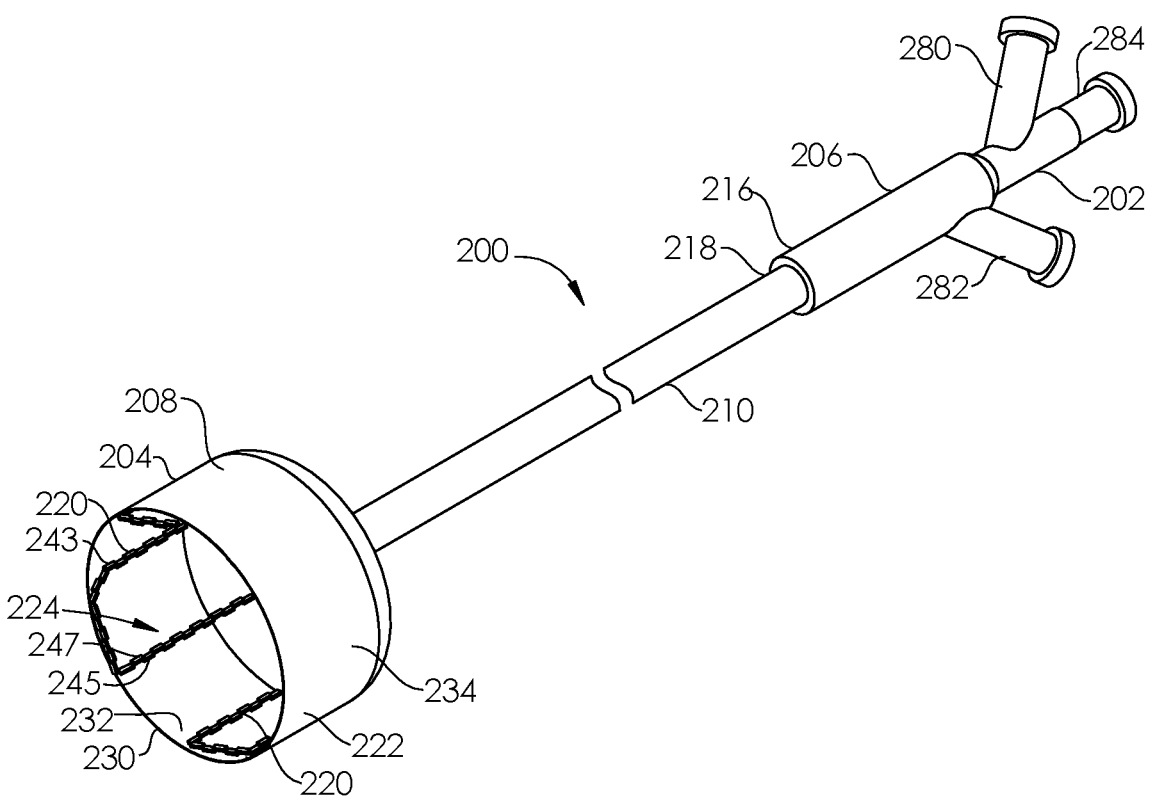
FIG. 22 is a perspective view of cooling probe according to a third embodiment of the present disclosure.
Figure 23:
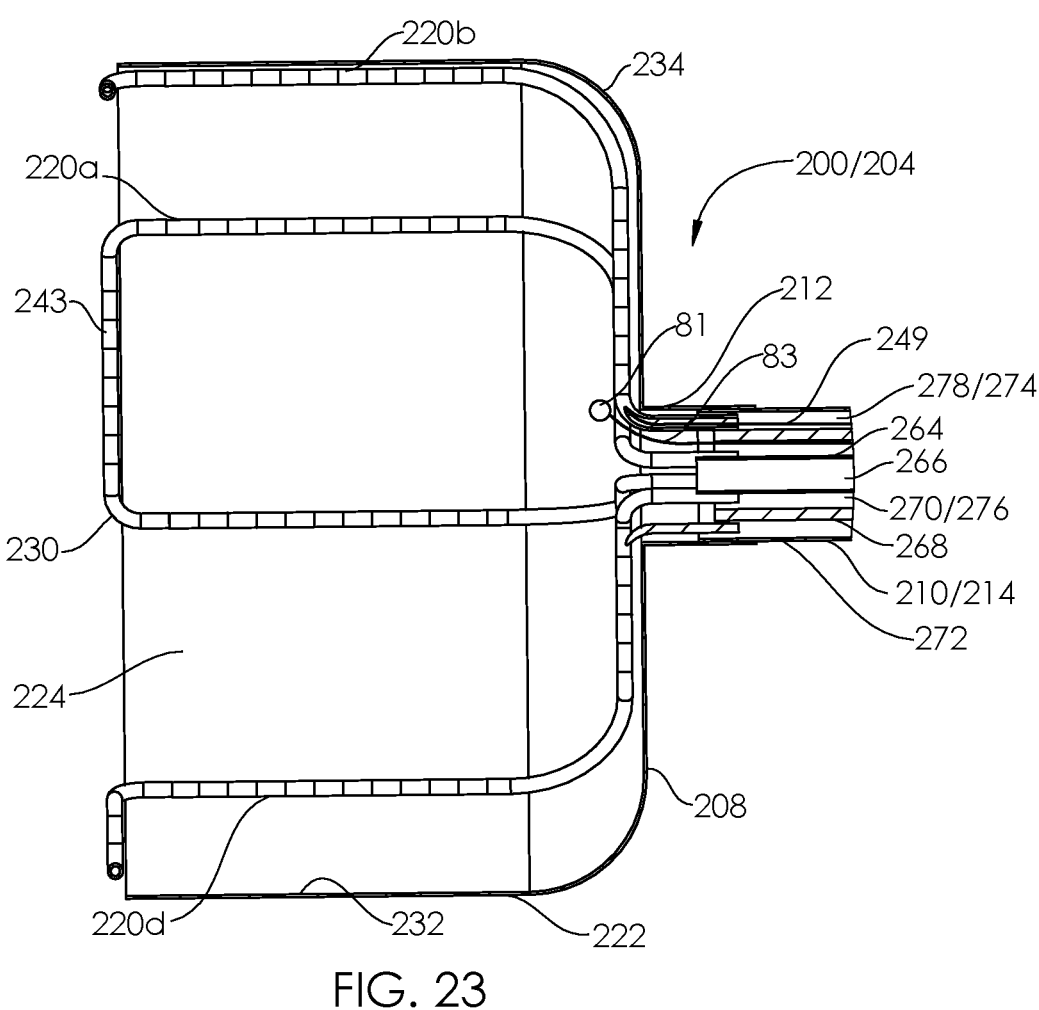
FIG. 23 is a longitudinal sectional view of the distal end of the cooling probe of FIG. 22.
Figure 24:
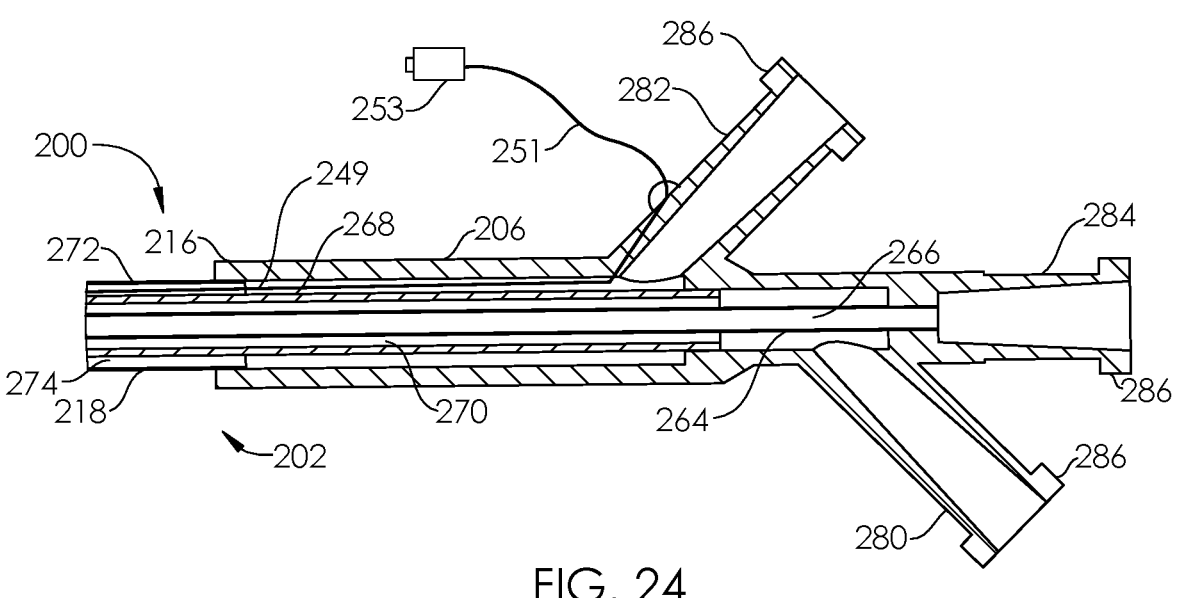
FIG. 24 is a longitudinal sectional view of the proximal connector of the cooling probe of FIG. 22.

FIG. 22 illustrates a cooling probe 200 configured for cooling tissue in a patient, including visceral fat. The cooling probe 200 is similar to the cooling probe 100 of FIG. 9, but the cooling tubes 120a-d have been replaced by expandable curves 220a-d comprising a plurality of miniature Peltier elements 243 or units. The miniature Peltier elements 243 each comprise a hot side junction 245 and a cold side junction 247. A temperature differential is electrically main- tained between the hot side junctions 245 and the cold side junctions 247. The cooling probe 200 comprises a proximal end 202 and a distal end 204, the proximal end 202 including a connector 206 and the distal end 204 including an expand- able cooling cup 208. An elongate shaft 210 is coupled to the cup 208 and the connector 206. As shown in FIG. 23, the proximal end 212 of the cup 208 is secured to a distal end 214 of the shaft 210, and as shown in FIG. 24, a distal end 216 of the connector 206 is secured to a proximal end 218 of the shaft 210. The cold side junctions 247 are arranged on the expandable curves 220a-d to selectively cool the con- tents (e.g. fat) within the interior 224 of the cup 208. The distal end 230 of the cup 208 is shown in FIG. 22, showing the inner surface 232 and outer surface 234 of the elastic cover 222, which may be coupled to the expandable curves 220a-d in the same manner as the elastic cover 122 may be couped to the cooling tubes 120a-d.

All of the components of the cooling probe 200 may be similar to those of the cooling probe 100, with the exception of the cooling tubes 120 and the manner that they are coupled to the fluid inlet lumen 170 and the fluid outlet lumen 174. The connector 206 includes a suction port 284 that is used with the suction lumen 266 in the same manner as the suction port 184 of the cooling probe 100, to pull fat into the interior 224 of the cup 208 using suction, so that the fat can be cooled by the cold side junctions 247 of the miniature Peltier elements 243. The inflow port 280 and outflow port 282 are not interconnected by intermediate tubes (e.g., cooling tubes 120), and thus they do not cooperatively recirculate fluid in a single fluid path. The inflow port 280, which may comprise a luer fitting 286, is configured for coupling to a warming fluid source. To avoid the cooling of the cup 208 and its contents to an undesirably low temperature (e.g., less than ~20° C.) by the miniature Peltier elements 243, warming fluid may be injected through the inflow port 280, which is hydraulically coupled to the fluid inlet lumen 270. The injection may be done by hand by the user, with a small-bore syringe. The user will be able to judge, via manual pressure/force feedback if the warming fluid can be injected without, for example, displacing the fat that has been suctioned into the interior 224 of the cup 208. The outflow port 282 is hydraulically coupled to the fluid outlet lumen 274. This port and lumen 282/274 may be utilized to aspirate any additional fluid, for example, blood that may be blocking the view of the laparoscope. They also may be utilized to inject other materials (cooling fluid, drugs, etc.), or may even be used as a secondary or backup suction line. Any of the ports 280, 282, 284 may comprise luer fittings 286, or alternative structures, as previously described in relation to ports 180, 182, 184. Outer tube 272 and intermediate tube 268 provide the annulus 278. Intermediate tube 268 and inner tube 264 provide the annulus 276.

The miniature Peltier elements 243 may comprise technology as described in United States Pat. App. Pub No. 2018/0008332, published on Jan. 11, 2018, and entitled "CATHETER WITH MICRO-PELTIER COOLING COMPONENTS," which is hereby incorporated by reference in its entirety for all purposes. The miniature Peltier elements 243 are coupled to and powered via conductor wires 249 (FIGS. 23-24), which may extend proximally through any of the lumens 284, 270, 274, or may be incorporated into any of the tube walls, as previously described. The conductor wire 249 is shown in FIG. 23 coupled to the expandable curves 220*a-d* comprising the plurality of miniature Peltier elements 243 and shown in FIG. 24 extending proximally through the fluid outlet lumen 274. A cable 251 connects to the conductor wire 249 and extends from the connector 206, terminating in an electrical connector 253. The cooling probe 200 may also incorporate the thermistor 81 (FIG. 23) for monitoring of temperature during cooling of fat within the interior 224 of the cup 208. Any of the following embodiments incorporating cooling tubes, may alternatively incorporate curved and/or expandable structures comprising a plurality of miniature Peltier elements 243 or units.

Figure 25:
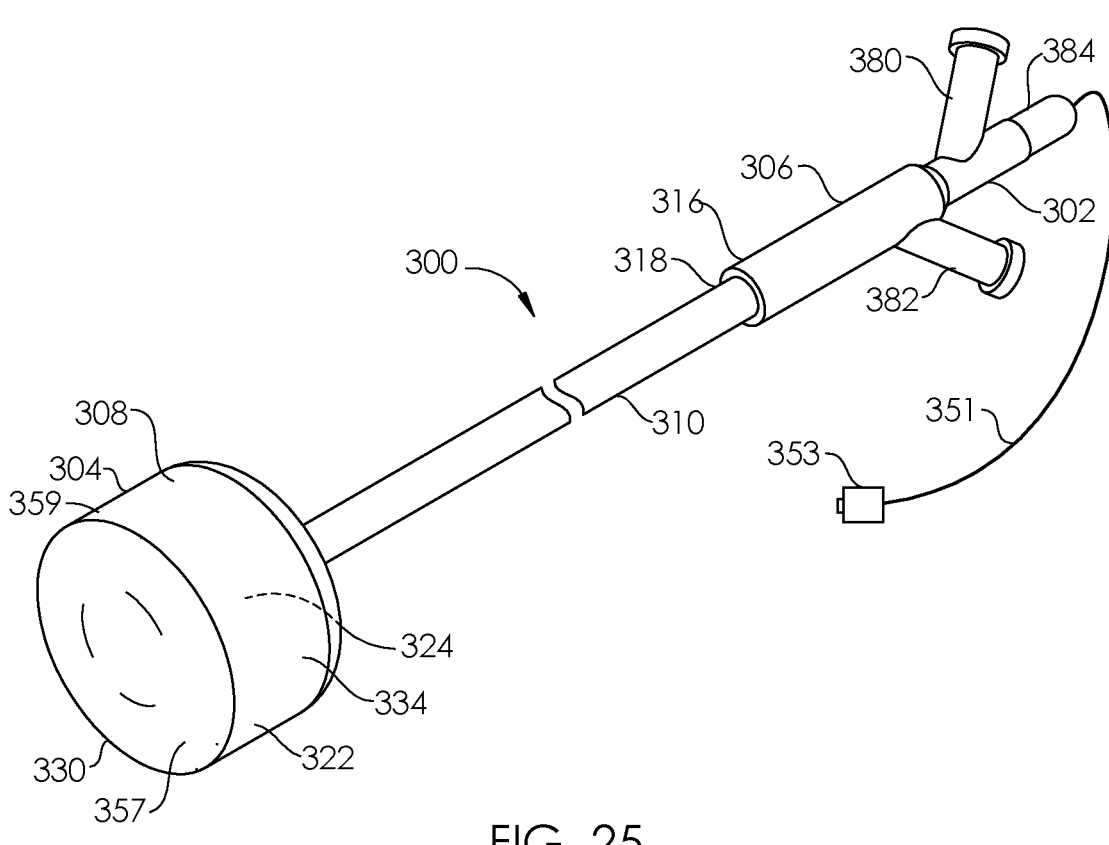
FIG. 25 is a perspective view of cooling probe according to a fourth embodiment of the present disclosure.

FIG. 25 illustrates a cooling probe 300 configured for cooling tissue in a patient, including visceral fat. The cooling probe 300 differs with the cooling probes 100 or the cooling probe 200 in that the distal end 304 comprises an expandable cooling balloon 308 carried on the distal end 314 of the elongate shaft 310, and does not utilize cooling tubes (or miniature Peltier elements). The proximal end 302 comprises a connector 306 configured for operating the cooling balloon 308. The distal end 316 of the connector 306 is secured to the proximal end 318 of the shaft 310. The proximal end 312 of the cooling balloon 308 is secured to the distal end 314 of the shaft 310. The cooling balloon 308 comprises an expandable membrane 322 comprising a compliant or semi-compliant material. In some embodiments, an elastomeric material is utilized. The distal end 330 of the cooling balloon 308 comprises a treatment surface 357, configured for contacting visceral fat to be cooled. Coolant is circulated into and out of the interior 324 of the cooling balloon 308 in order to promote heat exchange with the visceral fat being cooled. The cooling balloon 308 is also configured to be inflated by the coolant. Control of the inflow rate and the outflow rate (by an inflow pump and an outflow pump by the system 10) creates the positive pressure gradient required to inflate the balloon 308, and to maintain the inflation of the balloon 308, while also allowing coolant heated by the body tissue and fluids to be replaced by new chilled coolant. While the balloon is being inflated, the inflow rate of coolant tends to be greater than the outflow rate of coolant. While the inflated balloon is actively heat exchanging with the fat, the inflow rate and outflow rate tend to closely match each other. When the balloon is being deflated, the outflow rate tends to be greater than the inflow rate. The cooling probe 300 may also incorporate the thermistor 81 (FIG. 27) for monitoring of temperature of the coolant within the interior 324 of the balloon 308.

Figure 26:
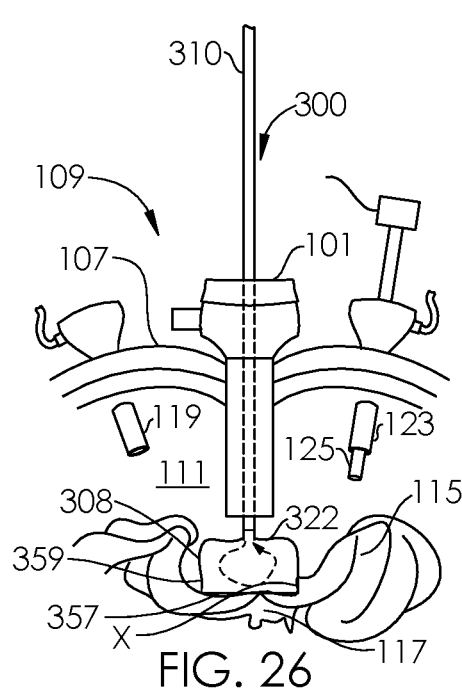
FIG. 26 is a perspective view of the cooling probe of FIG. 25 in an expanded configuration cooling visceral fat adjacent the small intestine.

The wall 355 of the balloon 308 comprises an inner surface 332 and an outer surface 334. In some embodiments, the balloon 308 may comprise a high-strength polymeric material such as polyimide, polyamide, or polyester (e.g., PET or PETG) to provide a thin wall 355 to optimize heat transfer. In some cases, at least a portion of the outer cylindrical portion 359 of the balloon 308 participates in the heat transfer with the adjacent tissue (e.g., fat). FIG. 26 illustrates the cooling probe 300 after it has been inserted through the first trocar 101 (with the balloon 308 uninflated) and into the abdominal cavity 111 of a patient 109. The coolant is shown circulating inside the subsequently inflated balloon 308 (dashed arrow) allowing heat transfer to occur with the visceral fat 117 at the treatment surface 357. Some of the outer cylindrical portion 359 also transfers heat with the visceral fat at location X. After the cooling procedure, the balloon 308 is allowed to deflate, and the cooling probe 300 is removed from the patient 109. The balloon 308 can be positioned such that the treatment surface 357 lies flat on an upper surface or upper layer of the visceral fat 117, to form a firm thermal contact with the tissue, for conductive heat transfer. By controlling the pressure gradient, the diameter of the balloon 308 can be controlled to achieve the desired balloon size in comparison with the treatment area.

Figure 27:
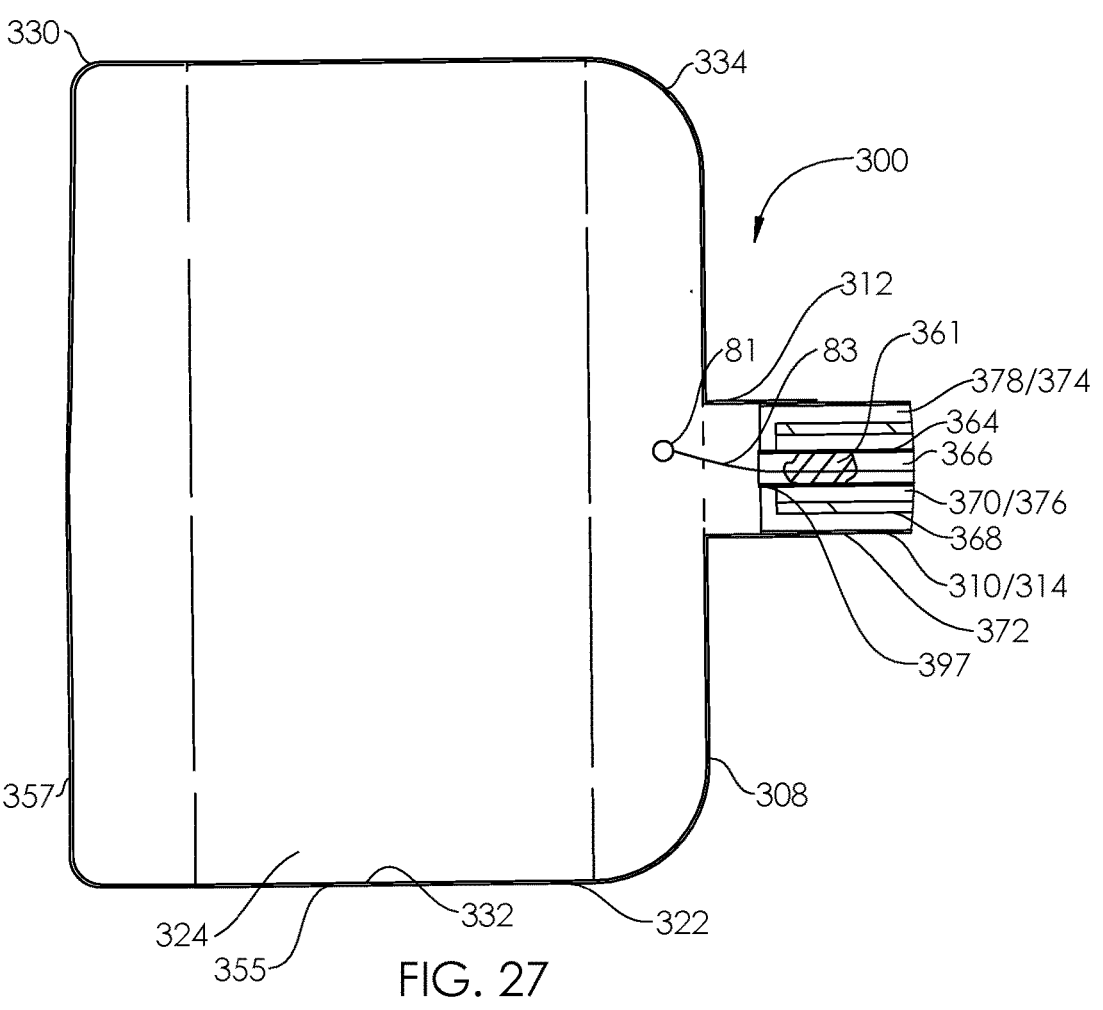
FIG. 27 is a longitudinal sectional view of the distal end of the cooling probe of FIG. 25.
Figure 28:
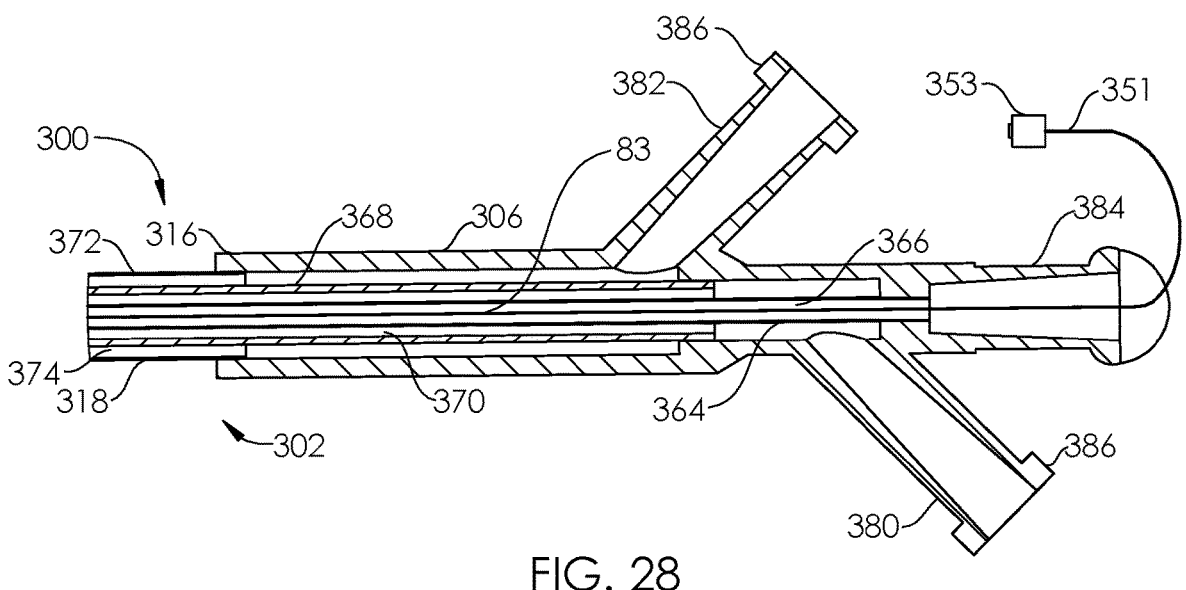
FIG. 28 is a longitudinal sectional view of the proximal connector of the cooling probe of FIG. 25.

Turning to FIGS. 27-28, because there is no suction of tissue in this embodiment, the lumen 366 of inner tube 364 serves as a conduit for the thermistor wire 83. At the distal end 397 of the inner tube 364, the thermistor wire 83 is bonded within the lumen 366 with adhesive or epoxy 361. The lumen may be intentionally blocked with the adhesive 361 to prevent any ingress of fluids. The thermistor wire 83 is also secured at the central extension 384 of the connector 306, and connected to a cable 351 extending to an electrical connector 353. As in the other embodiment described herein, a feedback loop from the signal sent by the thermistor 81 and received by the system 10 from the connector 353 can be programmed into the controller 74 (FIG. 2) to maintain a treatment temperature T of between about −20° C. and about +10° C., or where −20° C.<T<+10° C., or where −20° C.≤T≤+10° C., or where −20° C.≤T<+10° C., or where −20° C.<T≤+10° C. However, because the thermistor 81 of the cooling probe 300 is within the interior 324 of the balloon 308, the programmed temperature may be a lower calculated range. For example, a temperature range of between about −25° C. and about +5° C. within the balloon 308 may in some embodiments correspond with a treatment temperature at the visceral fat 117 of between about –20° C. and about +10° C.

The inflow port 380 and outflow port 382 are the beginning and end of a flow path within the cooling probe 300 that includes the fluid inlet lumen 370 (annulus 376), the interior 324 of the balloon 308, and the fluid outlet lumen 374 (annulus 378). Intermediate tube 368 and outer tube 372 are similar to those 168, 268, 172, 272 in the previous embodiments. The inflow port 380, which may comprise a luer fitting 386, is hydraulically coupled to the fluid inlet lumen 370 and is configured for coupling to pump for injecting coolant that has been cooled by a heat exchanger. The outflow port 382, which may comprise a luer fitting 386, is hydraulically coupled to the fluid outlet lumen 274 and returns "spent" coolant from the interior 324 of the balloon 308 to the heat exchanger for re-cooling.

Figure 29:
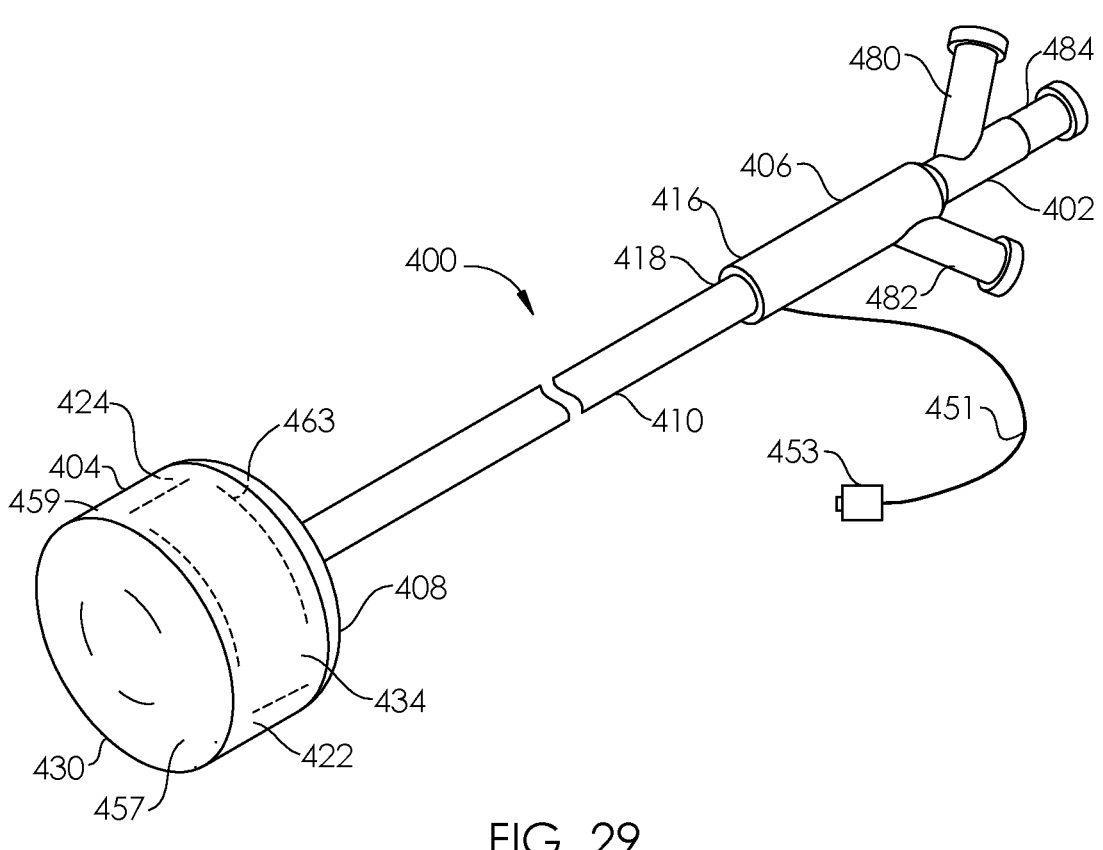
FIG. 29 is a perspective view of cooling probe according to a fifth embodiment of the present disclosure.
Figure 31:
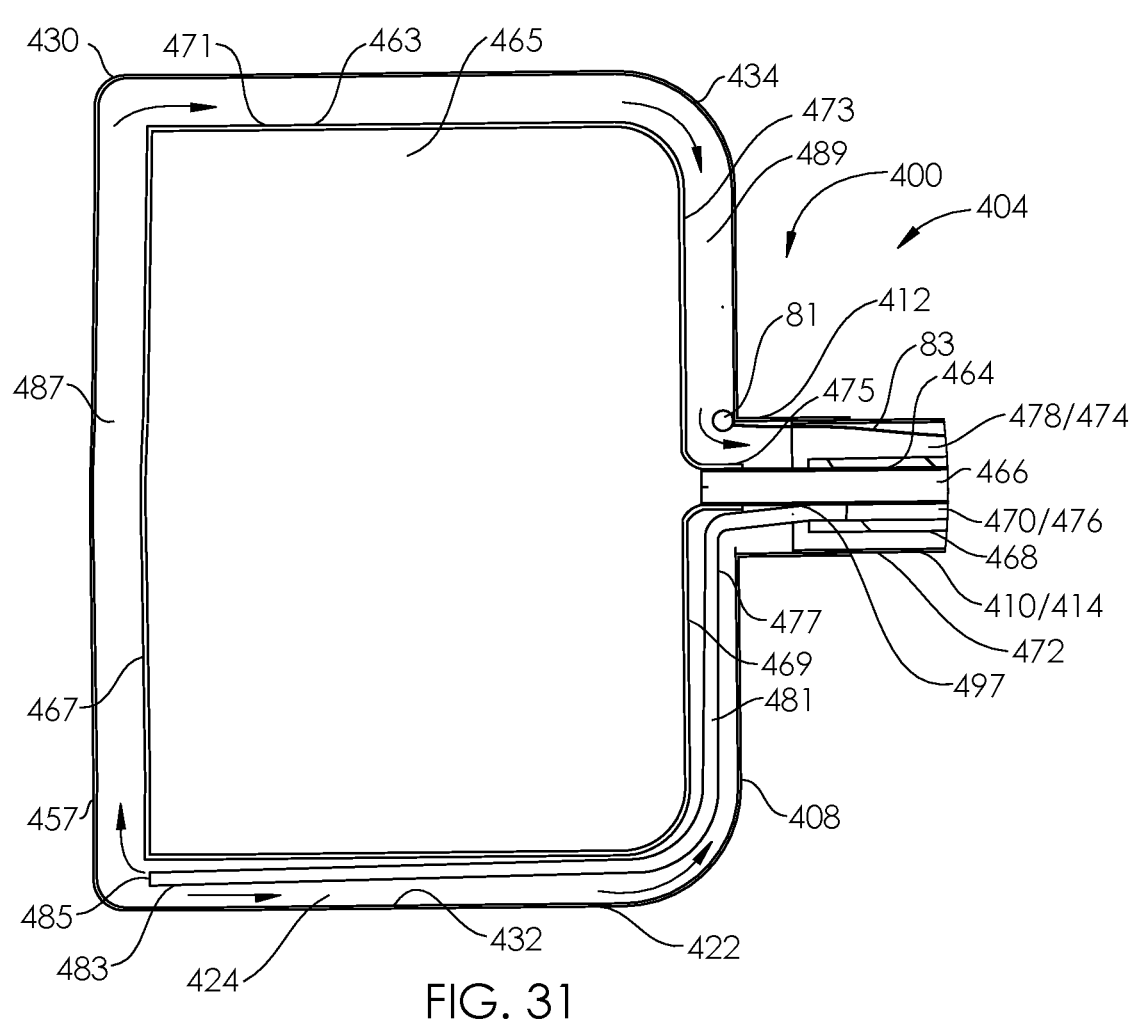
FIG. 31 is a longitudinal sectional view of the distal end of the cooling probe of FIG. 29.

FIG. 29 illustrates a cooling probe 400 configured for cooling tissue in a patient, including visceral fat. The cooling probe 400 comprises an expandable cooling balloon 408 carried on the distal end 414 of the elongate shaft 410, but the cooling balloon 408 differs from the cooling balloon 308 of the cooling probe 300 of FIG. 25 because the cooling balloon 408 comprises two chambers: an inner chamber to control the amount of inflation and an outer annular chamber to provide heat transfer with the body tissue. The proximal end 402 comprises a connector 406 configured for operating the cooling balloon 408. The distal end 416 of the connector 406 is secured to the proximal end 418 of the shaft 410. The proximal end 412 of the cooling balloon 408 is secured to the distal end 414 of the shaft 410. Turning to FIG. 31, the cooling balloon 408 comprises an inner balloon 463 comprising a non-compliant or semi-compliant material, such as polyimide, polyamide, or polyester (e.g., PET or PETG). The inner balloon 463 has a generally cylindrical interior 465 configured to be inflated to a target static pressure. The target inflation pressure may depend on the balloon material chosen, but in general the pressure is chosen at which the inner balloon 463 holds a consistent shape and size. In some embodiments, the target pressure may be between about 2 atmosphere and about 8 atmospheres. The inner balloon 463 includes a wall 469 comprising a distal transverse face 467, a cylindrical portion 471, and a proximal disk-shaped transverse portion 473 necking down to a collar 475. The collar 475 is bonded to the distal end 497 of the inner tube 464 (Adhesive, epoxy, heat bond, shrink bond).

The cooling balloon 408 further comprises an expandable membrane 422 comprising a compliant or semi-compliant material. In some embodiments, an elastomeric material is utilized. The distal end 430 of the expandable membrane 422 comprises a treatment surface 457, configured for contacting visceral fat to be cooled. Coolant is circulated into and out of a mostly annular interior 424 of the cooling balloon 408 that is between the outer diameter of the inner balloon 463 and the inner diameter of the expandable membrane 422. The most annular interior 424 (the space between the inner balloon 463 and the expandable membrane 422) is configured to circulate coolant past the inner surface 432 of the expandable membrane 422 in order to promote heat exchange of the outer surface 434 of the expandable membrane 422 with the visceral fat being cooled. The choice of a gas, such as air, $CO_2$, or nitrogen, to fill the interior 465 of the inner balloon 463 also serves as a thermal insulator so that the heat exchange is predominantly between the coolant flowing within the annular interior 424 and the fat or tissue externally adjacent the expandable membrane. Control of the inflow rate and the outflow rate (by an inflow pump and an outflow pump by the system 10) assures an appropriately matched flow of the coolant, and the maintenance of a generally constant pressure within the annular interior 424. The pressure of the coolant within the annular interior is generally at least slightly greater than the inflated pressure of the interior 465 of the inner balloon 463. The cooling probe 400 may also incorporate the thermistor 81 (FIG. 31) for monitoring of temperature of the coolant within the interior annular interior 424. In FIG. 31, the thermistor wire 83 is shown extending through the fluid outlet lumen 474 (annulus 478), though in other embodiments, it may instead extend through the fluid inlet lumen 470 (annulus 476).

Figure 32:
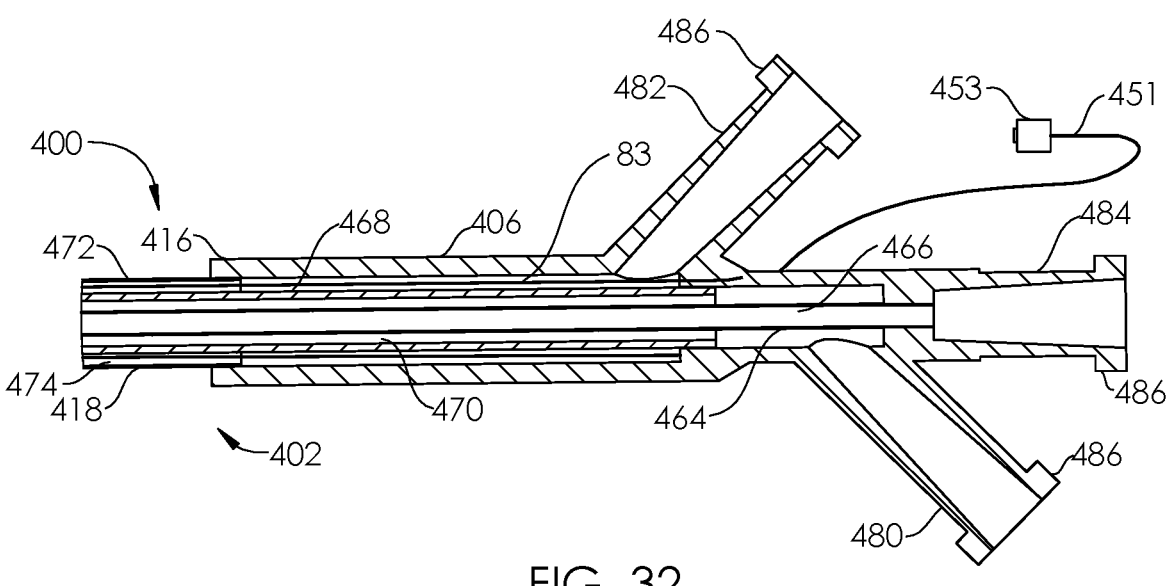
FIG. 32 is a longitudinal sectional view of the proximal connector of the cooling probe of FIG. 29.

Turning to FIG. 32, an inflation port 484, which may comprise a luer fitting 486, is configured for attaching a syringe or inflation device. The inflation lumen 466 of the inner tube 464 is hydraulically coupled to the inflation port 484 and carries the inflation media (e.g., gas or liquid) into the interior 465 of the inner balloon 463, to allow the inner balloon 463 to be inflated to the desired inflation pressure. The inflow port 480, which may comprise a luer fitting 486, is configured to couple to a supply of coolant (e.g., that has been cooled by a heat exchanger). The inflow port 480 is hydraulically coupled to the fluid inlet lumen 470 of the intermediate tube 468 (annulus 478). Turning to FIG. 31, at the distal end 404 of the cooling probe 400, a flexible feed tube 477 is hydraulically coupled to the fluid inlet lumen 470. The feed tube 477 may comprise a thin-walled polyimide or polyester tube, and has a relatively small diameter such that it can flex with the expansion or collapse of the balloon 408. The feed tube 477 has a proximal end 479 that is bonded within the annulus 476 such that its inner diameter 481 receives all or most of the coolant flow. The feed tube 477 has a distal end 483 having a distal opening 485. Thus, the coolant is selectively fed to a distal portion 487 of the interior 424 having a disc-shaped cross-section. The coolant then returns to a proximal portion 489 of the interior 424, moving in a substantially proximal direction (arrows). Thus, the coolant is able to traverse the interior 424 with a low start temperature, without undesired heating (heating that does not come from the heat exchange with the fat). The outflow port 482, which may comprise a luer fitting 486, is configured to receive the warmed coolant returning from the interior 424. The outflow port 482 is hydraulically coupled to the fluid outlet lumen 474 of the outer tube 472 (annulus 478).

The thermistor wire 83 is also secured at the side of the connector 406, and connected to a cable 451 extending to an electrical connector 453. As in the other embodiments described herein, a feedback loop from the signal sent by the thermistor 81 and received by the system 10 from the connector 453 can be programmed into the controller 74 (FIG. 2) to maintain a treatment temperature T of between about –20° C. and about +10° C., or where –20° C.<T<+10° C., or where –20° C.≤T≤+10° C., or where –20° C.≤T<+10° C., or where –20° C.<T≤+10° C. However, because the thermistor 81 of the cooling probe 400 is within the interior 424 of the expandable membrane 422, the programmed temperature may be a lower calculated range. For example, a temperature range of between about –25° C. and about +5° C. within the interior 424 may in some embodiments correspond with a treatment temperature at the visceral fat 117 of between about –20° C. and about +10° C.

Figure 30:
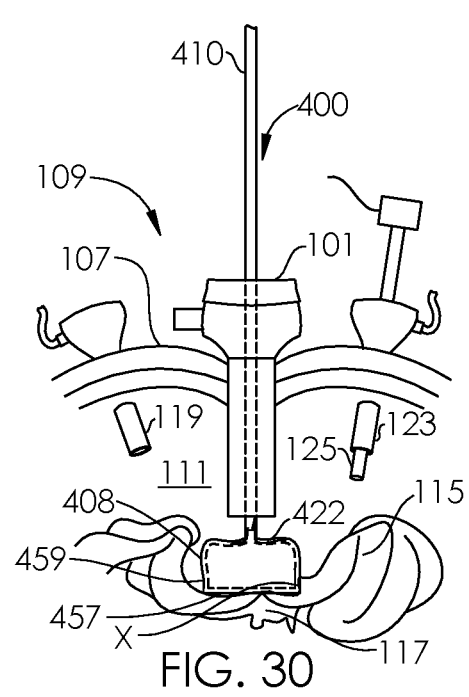
FIG. 30 is a perspective view of the cooling probe of FIG. 29 in an expanded configuration cooling visceral fat adjacent the small intestine.

In some cases, at least a portion of an outer cylindrical portion 459 of the expandable membrane 422 participates in the heat transfer with the adjacent tissue (e.g., fat). FIG. 30 illustrates the cooling probe 400 after it has been inserted through the first trocar 101 (with the balloon 408 uninflated) and into the abdominal cavity 111 of a patient 109. The coolant circulates inside the expandable membrane 422, allowing heat transfer to occur with the visceral fat 117 at the treatment surface 457. Some of the outer cylindrical portion 459 also transfers heat with the visceral fat at location X. After the cooling procedure, the coolant flow is stopped and the inner balloon 463 is deflated, and the cooling probe 400 is removed from the patient 109. The balloon 408 can be positioned such that the treatment surface 457 lies flat on an upper surface or upper layer of the visceral fat 117, to form a firm thermal contact with the tissue, for conductive heat transfer. The diameter of the expandable membrane 422 can be controlled to achieve the desired expanded size in comparison with the treatment area. The degree of expansion of the inner balloon 463 can also be adjusted, by changing pressure and/or diameter, to help achieve the desired size in comparison with the treatment area.

Figure 33:
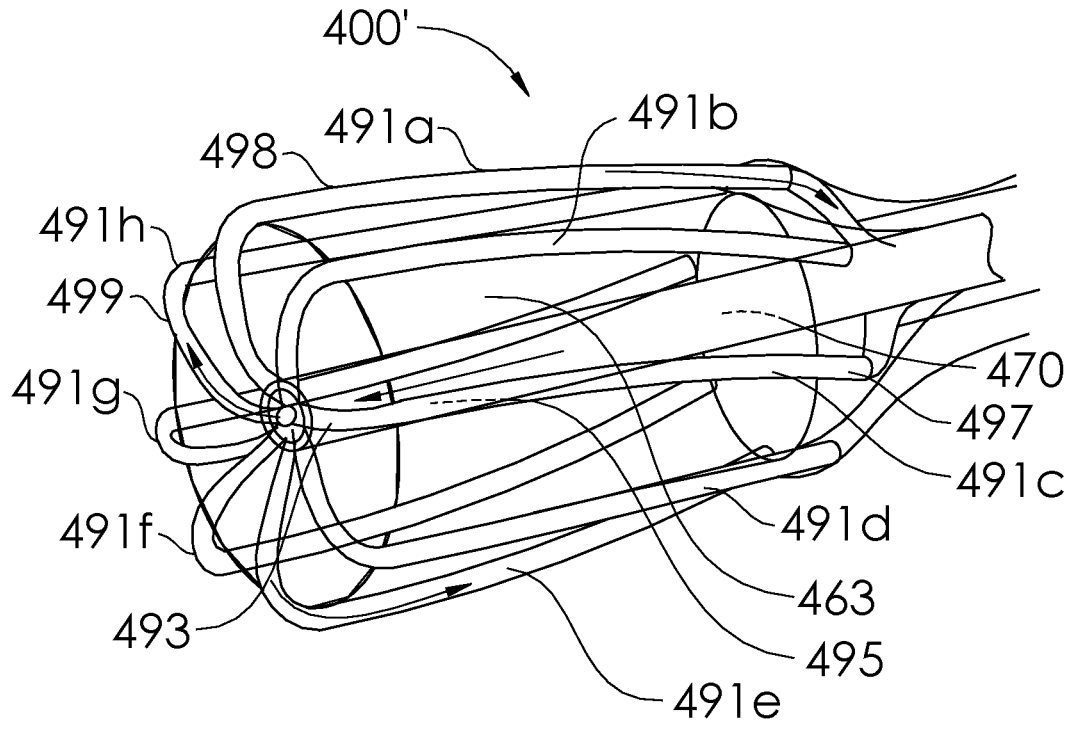
FIG. 33 is an alternative embodiment of the cooling probe of FIG. 29.

FIG. 33 illustrates an alternative embodiment of the cooling probe 400' wherein the expandable membrane 422 is removed and replaced by a series of eight spiral tubes 491*a-h* having a lumen 465. Each of the spiral tubes 491*a-h* is configured to be carried on the outer diameter of the inner balloon 463. Each of the first ends 493 of the spiral tubes 491 is hydraulically coupled to the fluid inlet lumen 470 by bonding. The fluid inlet lumen 470 may extend parallel to the inflation lumen 466, allowing the fluid inlet lumen 470 to extend to the distal end 404 of the cooling probe 400', as shown. The pressurized coolant thus is propelled radially at the distal end 404 and then proximally in a spiral manner having both circumferential and longitudinal components, toward the proximal end 412 of the inner balloon 463. In the embodiment of FIG. 33, there are eight spiral tubes, and each tube 491 traverses 45° circumferentially over the length of the inner balloon 463. Other numbers of tubes 491 and other amounts of spiraling are anticipated. The spiral shapes of the tubes 491 aid in the collapse and expansion of the tubes 491 in relation to the collapse and expansion of the inner balloon 463. Each of the second ends 497 of the spiral tubes 491 is hydraulically coupled to the fluid outlet lumen 474 by bonding. Thus, the front face 499 comprises an array of eight radially extending portions and the side 498 comprises a circumferential array of spiral portions both of which are capable of cooling adjacent tissue. In other embodiments, the spiral tubes 491*a-h* may be bonded to the inner balloon 463 at all surfaces, and may even be configured such that pressurization of the tubes can aid or cause the inflation of the inner balloon 463. This mechanical action may be compared to the stiffening and flexing of a Bourdon tube. In some embodiments, the expandable membrane 422 may be re-added to the probe 400' and configured to be carried over the spiral tubes 491*a-h*. The spiral tubes 491*a-h* may even be formed as a part of the expandable membrane 422 such that it is one composite structure, or even one integral structure having a series of channels. The shape of the tubes 491 or channels need not be spiral, and may simply be straight longitudinal, a single curve within a single plane, or multiple curves or a wavy or sinusoidal shape. In some embodiments, overall flow through the tubes 491 or channels may be substantially proximal to distal instead of substantially distal to proximal. In an alternative embodiment of the cooling probe 100 of FIG. 9 or the cooling probe 200 of FIG. 22, the cooling tubes 120 or the curves 220 may be also be configured into spiral shapes.

Figure 34:
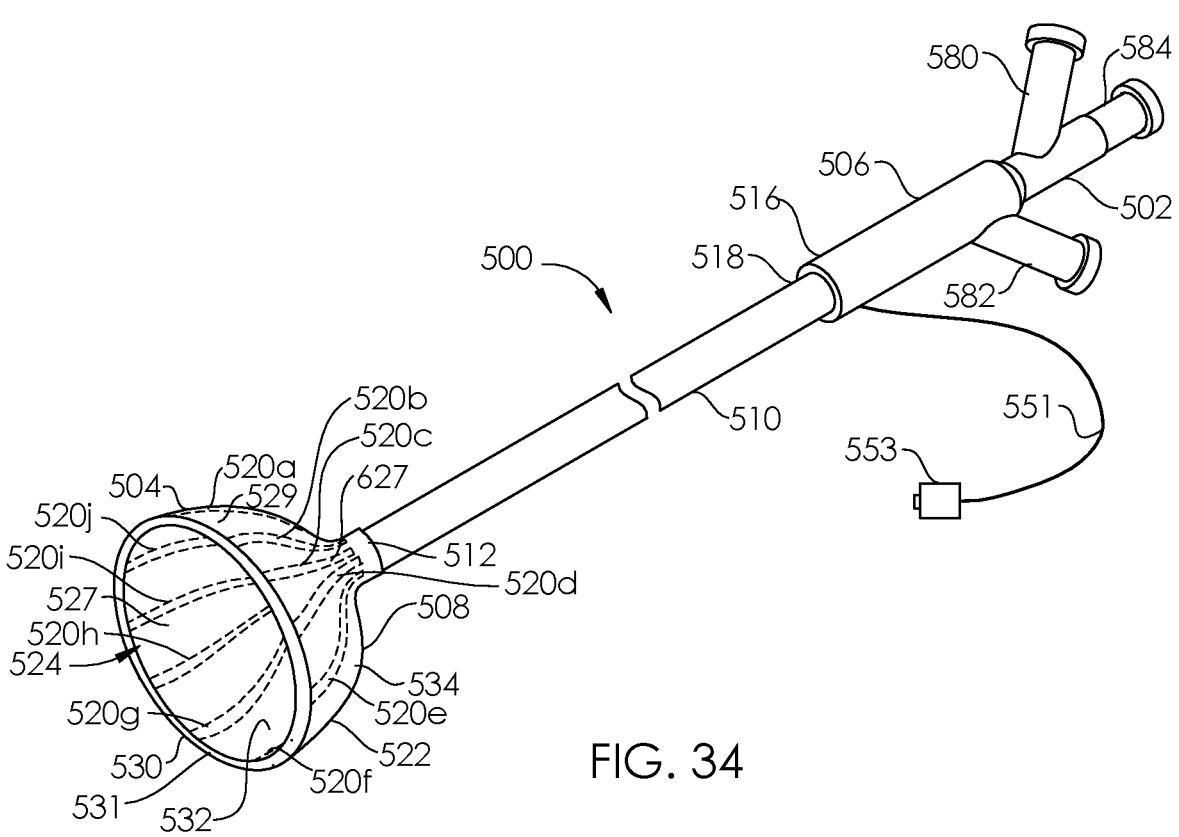
FIG. 34 is a perspective view of cooling probe according to a sixth embodiment of the present disclosure.

FIG. 34 illustrates a cooling probe 500 configured for cooling tissue in a patient, including visceral fat. The cooling probe 500 is similar to the cooling probe 100 of FIG. 9 or the cooling probe 200 of FIG. 22 in the manner that central suction is applied within a cooling cup. However, in the cooling probe 500, the cooling tubes 120*a-d*, 220*a-d* have been replaced by a combination of ten support wires 520*a-j* and a cup-shaped cooling balloon 508 attached to the shaft 510 at the distal end 504 of the probe 500. The cup-shaped cooling balloon 508 has an interior 524 configured for fat to be suctioned therewithin. The suction lumen 566 of the inner tube 564 is configured to apply a section to the interior 524 of the balloon 508, in a similar manner to the cooling probes 100, 200. The cooling balloon 508 comprises an outer expandable membrane 522 having an inner surface 532 and an outer surface 534. The distal end 530 of the balloon 508 comprises a circumferential fold 531 (see FIG. 36) on the outer expandable membrane 522. The outer expandable membrane 522 may comprise a compliant or semi-compliant polymeric material, or may comprise an elastomeric material. High-strength materials may be used, as previously discussed, to provide a thin wall and help maximize the heat transfer through the wall. The outer expandable membrane 522 comprises a cylindrical shape that is inverted at the circumferential fold 531 to create an inner layer 527 comprising the inner surface 532 and an outer layer 529 comprising the outer surface 534. The first end 601 of the outer expandable membrane 522 is bonded to a distal end 605 of the outer tube 572, and the second end 603 of the of the outer expandable membrane 522 to the distal end 597 of the inner tube 564. The bonds are on the outer circumference of the tubes 572, 564, but may alternatively be to the inner circumferences of either. The circumferential fold 531 and the bonds of the ends 601, 603 to the tubes 572, 564 thus creates a balloon interior 607.

Within the interior 607 of the outer expandable membrane 522 is an inner balloon 563, which may be made from similar materials to the outer expandable membrane 522. The inner balloon 563 is inverted at a circumferential fold 615. A first end 609 of the inner balloon 563 is bonded to a distal end 611 of the intermediate tube 568 at an outer circumference, and the second end 613 of the inner balloon 563 is bonded to the distal end 611 of the intermediate tube 568 at an inner circumference. The inversion of the inner balloon 563 thus creates an interior 617 of the inner balloon 563. The attachments of the outer expandable membrane 522 and of the inner balloon 563 within the outer expandable membrane forms a flow space 619 in the remaining space of the interior 607. A flow path for coolant is thus created as coolant pumped through the fluid inlet lumen 570 enters the flow space 619 at an entry annulus 621, circulates distally and outwardly radially (dashed arrow) to a flow reversal area 623 comprising a generally 180° turn. The flow from the entry annulus 621 to the flow reversal area 623 provides heat exchange with fat that has been suctioned into the interior 524 of the balloon 508 via the inner surface 532 of the expandable membrane 522. The warmed coolant then travels along the flow space 619 in a proximally and inwardly radially (solid arrow) past an exit annulus 625 and into the fluid outlet lumen 574. The direction of flow of the coolant, as in the other embodiments described herein, assures that the coolant is more protected from eating by the patient's body, and that the coolant passes by the fat as early as possible in the flow process. However, in any of the embodiments, it may be desired to alternatively apply the flow in a reverse manner to the lumens. For example, if the cup or balloon were significantly long and the contents included significant flow (e.g., arterial), then cross-flow heat exchange may actually be more efficient for overall efficiency, thus suggesting the use of flow in the opposite direction.

In some embodiments, the injection of the pressurized coolant may cause some or all of the expansion of the balloon 508 from its collapsed state into its expanded state. However, in the embodiment of the cooling probe 500 of FIG. 34, curved superelastic (e.g., nickel-titanium alloy) wires 520*a-j* are circumferentially arrayed around the longitudinal axis of the probe 500, and provide the expansion memory that causes both the inner balloon 563 and the outer expandable membrane 522 to expand and form the expanded state of the balloon 508 when delivered from the lumen of a trocar. The wires 520*a-j* support an umbrella-type support and expansion. The wires 520*a-j* in this particular embodiment are carried within the interior 617 of the inner balloon 563 (see FIG. 36). One advantage of this is that the wires 520*a-j* also maintain the general form of the inner balloon 563, without it requiring to be inflated (e.g., by an additional lumen). The wires 520*a-j* may be bonded or otherwise secured in place at their proximal ends 627 only, or may be bonded along their length to the inner and outer interior surfaces 629, 631 of the inner balloon 563, to further control the expansion of the inner balloon 563 and the amount or relative thinness to its material (to provide more patency for the flow space 619. However, in other embodiments, the additional lumen for the inner balloon 563 may be provided and the wires 520*a-j* may be carried within the flow space 619, or even on the inner surface 532 or outer surface 534 of the outer expandable membrane 522, or a combination of any of these. The inner balloon 563 in this embodiment may even be inflated with a coolant to maximize the amount of heat transfer at the beginning of the procedure. The wires 520*a-j* comprise flat wire (e.g. 0.005:×0.0015") but may alternatively comprise round wire. Though ten wires 520*a-j* are shown, other numbers of wires may be utilized, depending on the size and fit of the wires.

Figure 36:
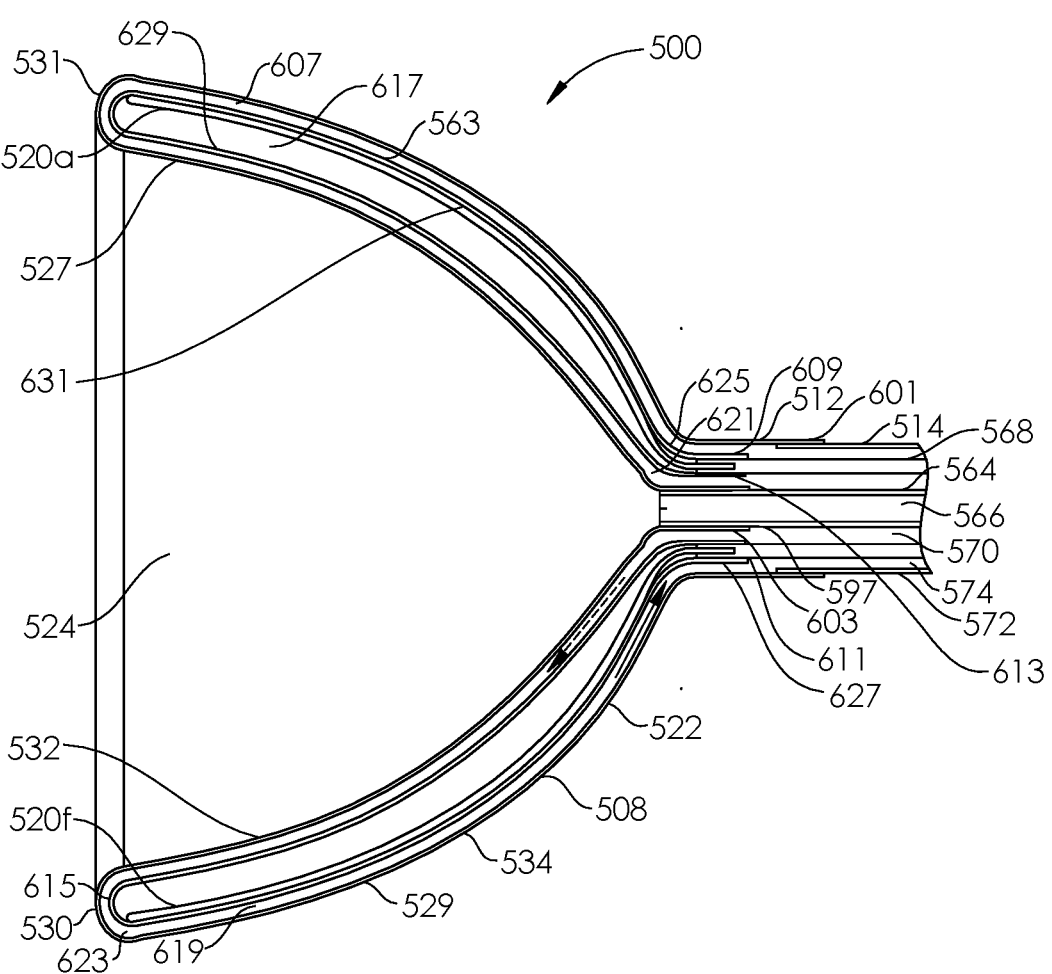
FIG. 36 is a longitudinal sectional view of the distal end of the cooling probe of FIG. 34.
Figure 37:
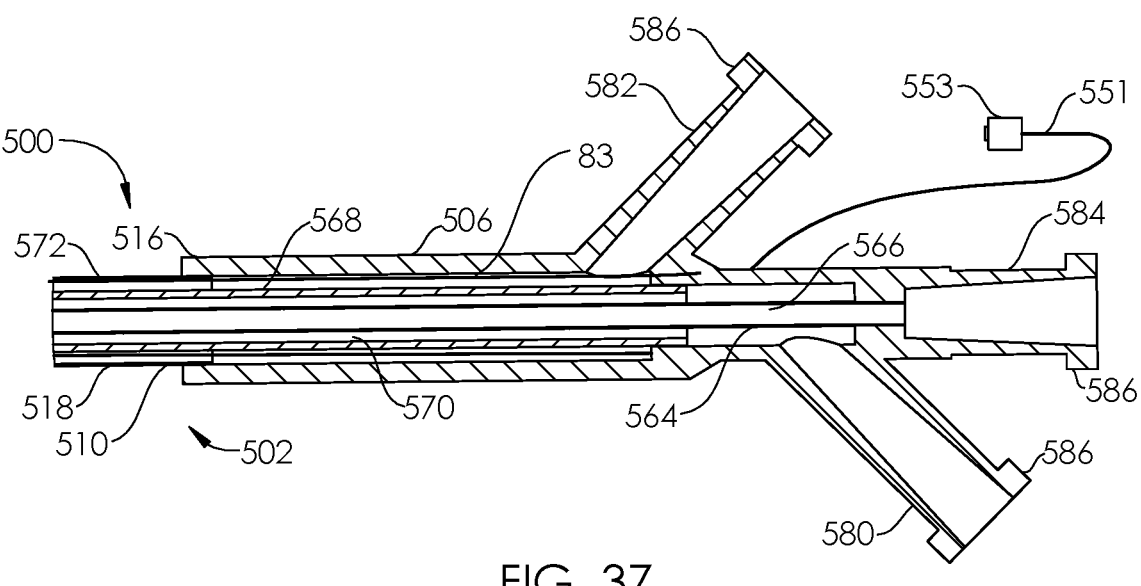
FIG. 37 is a longitudinal sectional view of the proximal connector of the cooling probe of FIG. 34.

Turning to FIGS. 36-37, the proximal end 502 comprises a connector 506 configured for operating the cup-shaped cooling balloon 508. The distal end 516 of the connector 506 is secured to the proximal end 518 of the shaft 510. The proximal end 512 of the cooling balloon 508 is secured to the distal end 514 of the shaft 510. The inner balloon 563 is configured to be inflated to a target static pressure. The target inflation pressure may depend on the balloon material chosen, but in general the pressure is chosen at which the inner balloon 563 holds a consistent shape and size. In some embodiments, the target pressure may be between about 2 atmosphere and about 8 atmospheres.

A suction port 584, which may comprise a luer fitting 586, is configured for attaching to a syringe or vacuum pump. The suction lumen 566 of the inner tube 564 is hydraulically coupled to the suction port 584 is configured to allow suction to be applied to the interior 524 of the balloon 508. The inflow port 580, which may comprise a luer fitting 586, is configured to couple to a supply of coolant (e.g., that has been cooled by a heat exchanger). The inflow port 580 is hydraulically coupled to the fluid inlet lumen 570 of the intermediate tube 568. The outflow port 582, which may comprise a luer fitting 586, is hydraulically coupled to the fluid outlet lumen 574 of the outer tube 572. The cooling probe 500 may in alternative embodiments incorporate the cooling tubes or channels of the cooling probe 400' of FIG. 33.

Figure 35:
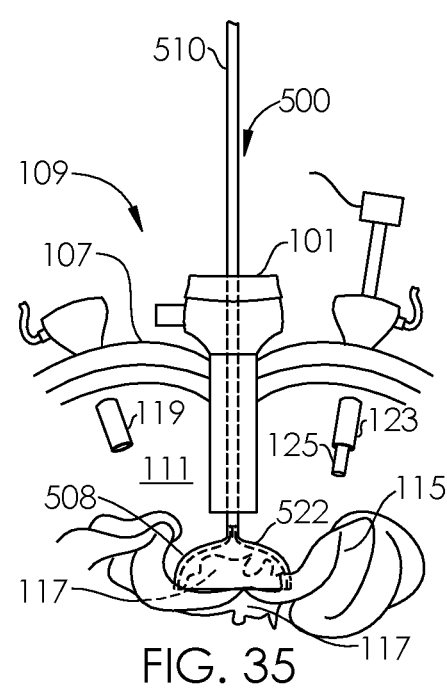
FIG. 35 is a perspective view of the cooling probe of FIG. 34 in an expanded configuration cooling visceral fat adjacent the small intestine.

FIG. 35 illustrates the cooling probe 500 after it has been inserted through the first trocar 101 (which causes the wires 520*a-j* to be temporarily collapsed within the trocar lumen)

and into the abdominal cavity 111 of a patient 109. The coolant circulates inside the flow space 619, allowing heat transfer to occur with the visceral fat 117 at the inner surface 532. Some of the outer surface 534 may also transfer heat with outer adjacent visceral fat. After the cooling procedure, the coolant flow is stopped and the inner balloon 563 is deflated, and the cooling probe 500 is removed from the patient 109. The diameter of the balloon 508 can be controlled to achieve the desired expanded size in comparison with the treatment area.

Thought the thermistor 81 is not shown in FIG. 36, it can be incorporated into this embodiment or any of the embodiments of cooling probes presented herein. The thermistor wire 83 is also secured at the side of the connector 506, and connected to a cable 551 extending to an electrical connector 553. As in the other embodiments described herein, a feedback loop from the signal sent by the thermistor 81 and received by the system 10 from the connector 553 can be programmed into the controller 74 (FIG. 2) to maintain a treatment temperature T of between about −20° C. and about +10° C., or where −20° C.<T<+10° C., or where −20° C.≤T≤+10° C., or where −20° C.≤T<+10° C., or where −20° C.<T≤+10° C. Other ranges can be used, as previously described.

Figure 38:
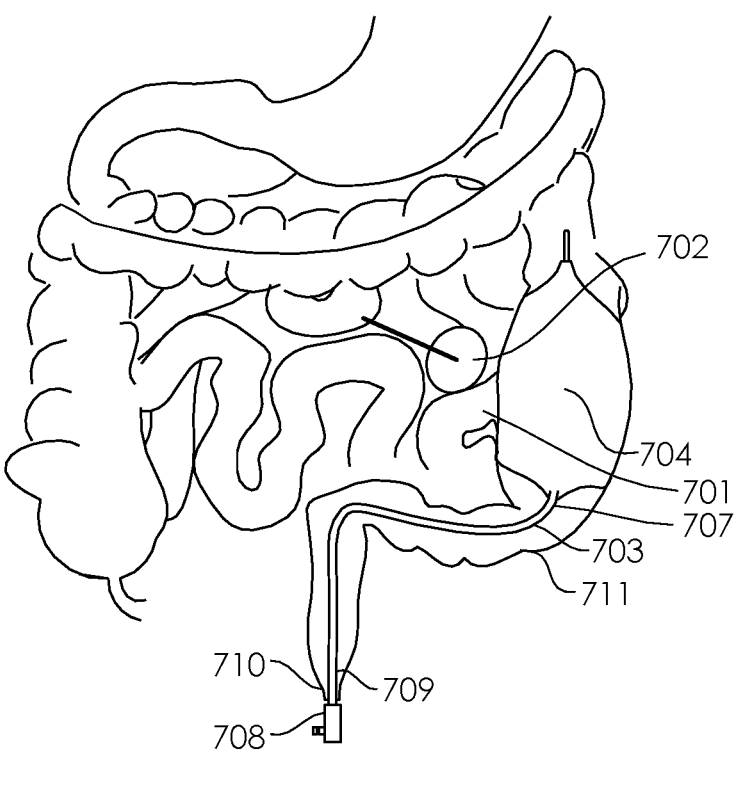
FIG. 38 is a plan view of a warming balloon being used with a cooling probe, according to an embodiment of the present disclosure.

Adjunctively, with the use of any of the cooling probes described herein, a warming balloon 704 may also be utilized to protect the normal tissue (e.g., non-fat tissue) adjacent the cooling area. FIG. 38 illustrates a warming balloon 704 attached to a distal end 707 of a hollow shaft 703. A connector 708 is attached to a proximal end 709 of the shaft 703. The connector 708 is configured to coupled to a heat exchange fluid source such that warmed fluid can be injected down an interior lumen of the shaft 703 and through the warming balloon 704. The fluid may be controlled by an external heater so that is enters the interior of the warming balloon at a temperature of between 37° C. and 42° C. The collapsed warming balloon 704 is first inserted into the anus 710 and colon 711 (as shown) or alternatively, the esophagus. The warming balloon 704 is then advanced until it is positioned adjacent the area to be treated by the cooling probe 702. The cooling probe 702 is then used to cool the fat to the desired temperature, while the warming balloon 704 adds extra safety to the adjacent tissue (e.g., intestine, stomach, esophagus), to better assure that damage will not occur.

Alternatively, the warming balloon 704 may be used as an adjunctive cooling device by circulating cooling fluid through it. Thus, cooling provided by the cooling probe 702 is augmented by the cooling from the warming (cooling) balloon 704.

While the foregoing is directed to embodiments of the present disclosure, other and further embodiments may be devised without departing from the basic scope thereof. In any of the embodiments described, the cooling probes may be alternatively configured for heating instead of cooling. For example, the probes may be configured to heat body tissue, including but not limited to fat, in order to at least partially deactivate it. The cooling probes described herein may alternatively be delivered to various locations of the body, including lumens of the body, without the use of laparoscopy and without the use of trocars for access. In any of the embodiments presented, the thermistor, or any temperature sensor, may be configured to be within the suction cup or otherwise externally carried at or adjacent the distal end in order to measure the temperature of the fat more directly.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. A system for laparoscopic thermal treatment of visceral fat, comprising:

an elongate cooling probe; a cooling fluid source; and a negative pressure source;

said probe comprising:

an elongate shaft having a proximal end and a distal end and having a maximum transverse dimension, the shaft having a suction lumen extending between its proximal end and distal end;

an expandable cup having a proximal end and a distal end, and comprising a collapsed state configured for placement through a channel of a trocar and an expanded state, the expanded state having a maximum outer diameter and a maximum inner diameter, the maximum inner diameter of the cup being larger than the maximum transverse dimension of the shaft, wherein the distal end of the cup in its expanded state defines an opening, and the cup in its expanded state defines an open interior space and is characterized by an inner surface, wherein the proximal end of the cup is coupled to the distal end of the shaft such that the suction lumen of the shaft is in fluid communication with the open interior space of the cup, and wherein the proximal end of the shaft is coupled to the negative pressure source, said negative pressure source operable to draw adipose tissue adjacent the opening of the cup into the interior of the cup; and one or more cooling elements disposed on an interior surface of the cup and configured to cool the adipose tissue within the interior of the cup; and wherein the probe further comprises a cooling fluid lumen within the elongate shaft, said cooling fluid lumen in fluid communication with the cooling fluid source; and the one or more cooling elements comprise one or more cooling tubes in fluid communication with the cooling fluid lumen.

2. The system of claim 1, wherein the cup comprises an elastic membrane having an inner surface and an outer surface.

3. The system of claim 2, wherein the inner surface of the elastic membrane is secured to the one or more cooling elements.

4. The system of claim 2, wherein the outer surface of the elastic membrane is secured to the one or more cooling elements.

5. The system of claim 2, wherein the inner surface of the elastic membrane is secured to one or more ribs.

6. The system of claim 2, wherein the outer surface of the elastic membrane is secured to one or more ribs.

7. The system of claim 1, wherein:

the one or more cooling elements comprise one or more Peltier junctions.

8. The system of claim 7, wherein the cup comprises an elastic membrane having an inner surface and an outer surface.

9. A system for laparoscopic thermal treatment of visceral fat, comprising:

an elongate cooling probe and a negative pressure source;

said probe comprising:

an elongate shaft having a proximal end and a distal end and having a maximum transverse dimension, the shaft having a suction lumen extending between its proximal end and distal end;

an expandable cup having a proximal end and a distal end, and comprising a collapsed state configured for placement through a channel of a trocar and an expanded state, the expanded state having a maximum outer diameter and a maximum inner diameter, the maximum inner diameter of the cup being larger than the maximum transverse dimension of the shaft, wherein the distal end of the cup in its expanded state defines an opening, and the cup in its expanded state defines an open interior space and is characterized by an inner surface, wherein the proximal end of the cup is coupled to the distal end of the shaft such that the suction lumen of the shaft is in fluid communication with the open interior space of the cup, and wherein the proximal end of the shaft is coupled to the negative pressure source, said negative pressure source operable to draw adipose tissue adjacent the opening of the cup into the interior of the cup; and one or more cooling elements disposed on an interior surface of the cup and configured to cool the adipose tissue within the interior of the cup;

wherein the cup comprises an inflatable balloon; and wherein the balloon comprises an inner layer and an outer layer, the outer layer having an outer surface, and a circumferential fold between the inner layer and the outer layer, extending around the opening of the distal end of the cup.

10. The system of claim 9, wherein the inner layer of the balloon is secured at a plurality of locations such that inflation of the balloon does not cause the inner layer to significantly expand inwardly, thus preserving the patency of the interior of the cup when the balloon is expanded.

11. The system of claim 10, wherein an internal surface of the inner layer of the balloon is secured directly to an internal surface of the outer layer of the balloon at one or more of the plurality of locations.

12. The system of claim 10, wherein an internal surface of the inner layer of the balloon is secured to one or more of the one or more cooling elements at one or more of the plurality of locations.

13. The system of claim 10, wherein an internal surface of the inner layer of the balloon is secured to one or more ribs extending along a surface of the cup from the proximal end of the cup to the distal end of the cup at one or more of the plurality of locations.

14. The system of claim 13, wherein the balloon maintains a particular inflated shape defining the expanded state of the cup by the securement of the internal surface of the inner layer of the balloon to the one or more ribs at the plurality of locations.

15. A system for laparoscopic thermal treatment of visceral fat, comprising:

an elongate cooling probe, a cooling fluid source, and a negative pressure source;

said probe comprising:

an elongate shaft having a proximal end and a distal end and having a maximum transverse dimension, the shaft having a suction lumen extending between its proximal end and distal end;

an expandable cup having a proximal end and a distal end, and comprising a collapsed state configured for placement through a channel of a trocar and an expanded state, the expanded state having a maximum outer diameter and a maximum inner diameter, the maximum inner diameter of the cup being larger than the maximum transverse dimension of the shaft, wherein the distal end of the cup in its expanded state defines an opening, and the cup in its expanded state defines an open interior space and is characterized by an inner surface, wherein the proximal end of the cup is coupled to the distal end of the shaft such that the suction lumen of the shaft is in fluid communication with the open interior space of the cup, and wherein the proximal end of the shaft is coupled to the negative pressure source, said negative pressure source operable to draw adipose tissue adjacent the opening of the cup into the interior of the cup; and one or more cooling elements disposed on an interior surface of the cup and configured to cool the adipose tissue within the interior of the cup; and wherein the probe further comprises a cooling fluid inlet lumen and a cooling fluid outlet lumen within the elongate shaft, said cooling fluid inlet lumen in fluid communication with the cooling fluid source; and the cup comprises a cup-shaped cooling balloon attached to the shaft, with an inner balloon disposed within the cup-shaped balloon defining a flow space for cooling fluid between the inner balloon and the cooling balloon, from the cooling fluid inlet lumen and the cooling fluid outlet lumen.

16. The system of claim 15, wherein the cup comprises an elastic membrane having an inner surface and an outer surface.

* * * * *